United States Patent
Gaisford et al.

[11] Patent Number: 6,157,015
[45] Date of Patent: *Dec. 5, 2000

[54] MICROWAVE HEATING APPARATUS FOR GAS CHROMATOGRAPHIC COLUMNS

[75] Inventors: Scott Gaisford, Denver; David L. Walters, Northglenn, both of Colo.

[73] Assignee: MT Systems, LLC, Denver, Colo.

[*] Notice: This patent is subject to a terminal disclaimer.

[21] Appl. No.: 09/359,879

[22] Filed: Jul. 23, 1999

Related U.S. Application Data

[63] Continuation-in-part of application No. 09/262,230, Mar. 4, 1999.

[51] Int. Cl.$^7$ ............... H05B 6/80; H05B 6/72; G01N 30/02
[52] U.S. Cl. ............ 219/748; 219/750; 219/679; 73/23.35; 95/87; 422/21
[58] Field of Search ................... 219/745, 746, 219/748, 749, 750, 679, 678, 690, 695, 696, 686; 73/23.35; 95/82, 87; 422/89, 21

[56] References Cited

U.S. PATENT DOCUMENTS

| | | |
|---|---|---|
| 3,023,835 | 3/1962 | Brashear . |
| 3,169,389 | 2/1965 | Green, Jr. et al. . |
| 3,232,093 | 2/1966 | Burow et al. . |
| 3,527,567 | 9/1970 | Philyaw et al. . |
| 4,204,423 | 5/1980 | Jordan . |
| 4,339,648 | 7/1982 | Jean . |
| 4,347,216 | 8/1982 | Kawasaki et al. . |
| 4,861,556 | 8/1989 | Neas et al. . |
| 4,882,286 | 11/1989 | Neas et al. . |
| 4,904,450 | 2/1990 | Floyd . |
| 4,923,486 | 5/1990 | Rubey . |
| 5,005,399 | 4/1991 | Holtzclaw et al. . |
| 5,009,099 | 4/1991 | Wells et al. . |
| 5,022,756 | 6/1991 | Rhodes . |
| 5,028,243 | 7/1991 | Rubey . |
| 5,066,843 | 11/1991 | Revesz . |
| 5,114,439 | 5/1992 | Yost et al. . |
| 5,131,993 | 7/1992 | Suib et al. . |
| 5,314,664 | 5/1994 | Sperling et al. . |
| 5,377,426 | 1/1995 | Pare . |
| 5,427,741 | 6/1995 | Bennett . |
| 5,443,795 | 8/1995 | Revesz . |
| 5,447,052 | 9/1995 | Delaune et al. . |
| 5,471,037 | 11/1995 | Goethel et al. . |
| 5,519,947 | 5/1996 | Pare . |
| 5,589,630 | 12/1996 | Wiegand et al. . |
| 5,611,846 | 3/1997 | Overton et al. . |
| 5,663,488 | 9/1997 | Wang et al. . |
| 5,675,909 | 10/1997 | Pare . |
| 5,744,696 | 4/1998 | Wang et al. . |
| 5,808,178 | 9/1998 | Rounbehler et al. . |

*Primary Examiner*—Philip H. Leung
*Attorney, Agent, or Firm*—Dorr, Carson, Sloan & Birney, P.C.

[57] ABSTRACT

A microwave heating apparatus is used for heating a chromatographic column assembly containing a microwave absorbing material. The microwave heating apparatus includes an antenna transmitting a microwave signal and a resonant cavity containing the chromatographic column assembly and the antenna. The chromatographic column assembly extends relative to predetermined electromagnetic field strength contours within the resonant cavity to provide a predetermined heating profile along the length of the chromatographic column assembly. For example, a single-mode chromatographic column microwave oven can be used to heat a coiled chromatography column to a desired temperature gradient along its length. Oven design embodiments utilizing coaxial transmission line structures, coaxial resonators, and cylindrical resonators are described. To control the electromagnetic field gradient in the axial direction, the oven designs provide for varying some part of the oven geometry in the axial direction. For best operation, vacuum conditions should be established within the oven during heating cycles.

29 Claims, 23 Drawing Sheets

*Fig. 9*
TM010 Resonator
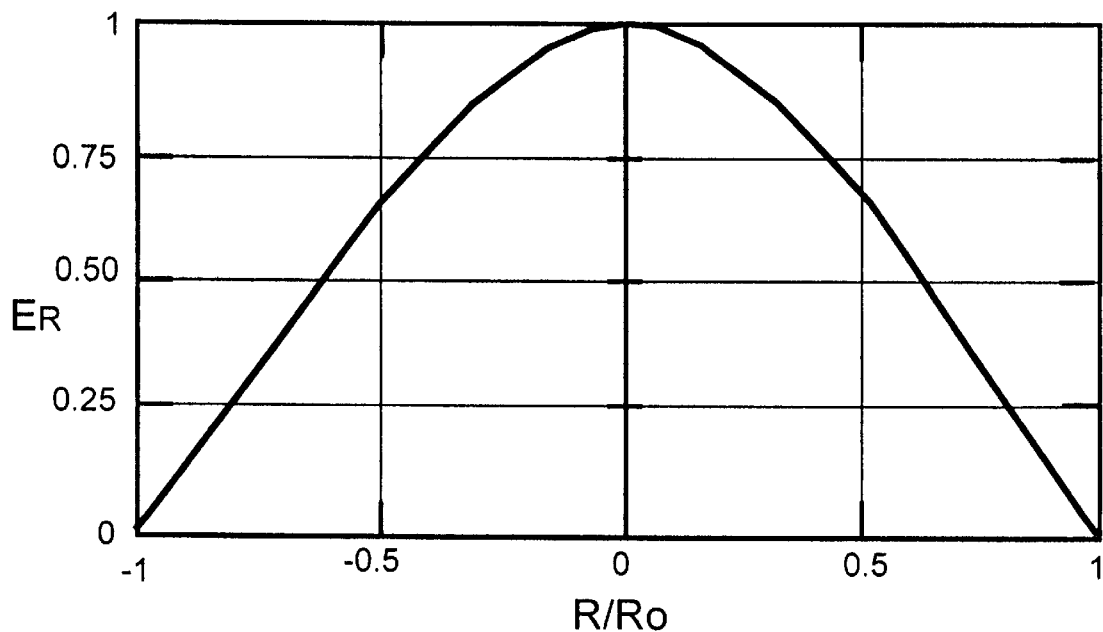
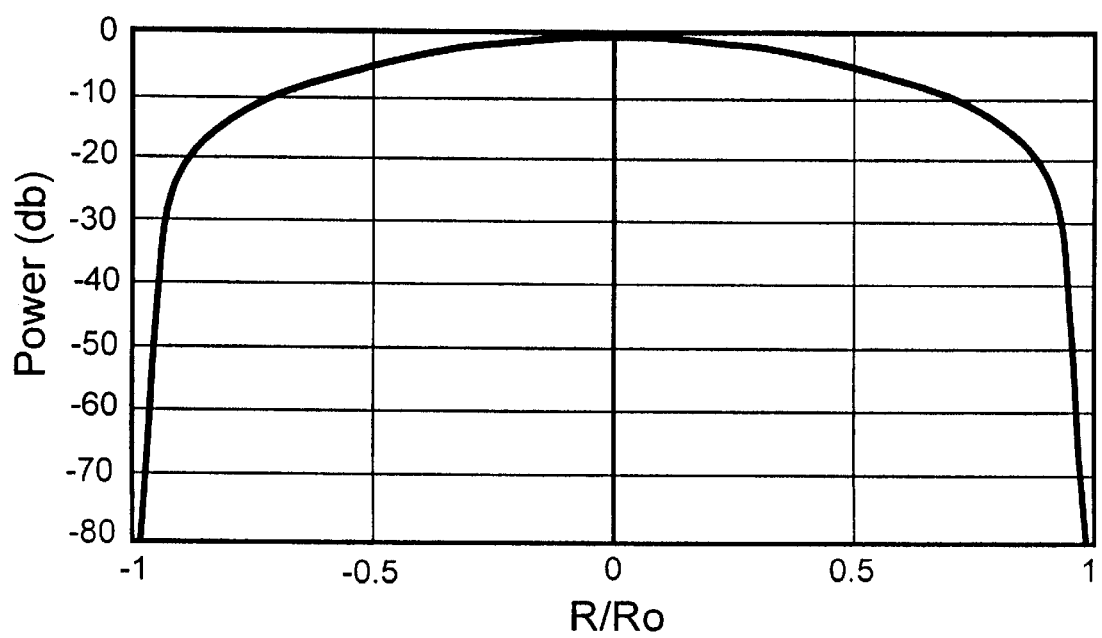
*Fig. 10*

Linear Column Temperature Profile

Periodic Column Temperature Profile

MICROWAVE HEATING APPARATUS FOR GAS CHROMATOGRAPHIC COLUMNS

RELATED APPLICATION

The present application is a continuation-in-part of the Applicants' co-pending U.S. patent application Ser. No. 09/262,230, entitled "Microwave Heating Apparatus For Gas Chromatographic Columns," filed on Mar. 4, 1999.

BACKGROUND OF THE INVENTION

1. Field of the Invention

The invention relates generally to the field of gas chromatography and specifically to the design of microwave heating apparatuses for heating a chromatographic column to achieve a controlled temperature profile along the length of the column.

2. Statement of the Problem

Gas chromatography is a physical method for the separation, identification, and quantification of chemical compounds. This method is used extensively for applications that include the measurement of product purity in analytical chemistry, the determination of environmental contamination, the characterization of natural substances, and the development of new products and processes.

A sample mixture to be analyzed in a gas chromatograph (GC) is injected into a flowing neutral carrier gas stream and the combination then flows through the chromatographic column. The inner surface of the column is coated with a material called the stationary phase. As the sample mixture and carrier stream flow through the column, the components within the mixture are retained by the stationary phase to a greater or lesser degree depending on the relative volatility of the individual components and on their respective affinities for the stationary phase. When the individual mixture components are released into the carrier stream by the stationary phase, they are swept towards the column outlet where they are detected and measured with a detector. Different chemical compounds are retained for different times by the stationary phase. By measuring the retention times, the specific compounds in the mixture can be identified. The relative concentration of the compounds is determined by comparing the peak amplitudes measured with the detector for each compound.

GC measurements are facilitated by the application of heat to the chromatographic column to change its temperature. The use of a heated column oven in gas chromatographic systems greatly increases the number of compounds that can be analyzed and speeds up the time required for each analysis by increasing the volatility of higher molecular weight compounds.

Many methods have been described for heating chromatographic columns. The simplest and most commonly used method utilizes resistive heating elements to heat air which is in turn circulated through an insulated oven in which the column is placed. For example, U.S. Pat. No. 3,527,567 to Philyaw et al. describes a GC oven heated with resistive elements.

The resistive element heating method has several limitations. To achieve even heating of the column, a large volume of air is rapidly circulated around the chromatographic column. In addition to heating the column, the air heats the oven itself. Because the thermal mass of the oven is much larger than that of the column, the rate at which the column can be heated is commensurately reduced. A related problem is cooling time. After heating the oven to a high temperature during an analysis, it takes significantly longer to cool the oven plus the column to their initial temperature so that the next sample may be analyzed than it would to cool the column alone. Together, these limitations reduce the throughput of the chromatograph.

Attempts to localize the resistive heat element onto the column itself so as to reduce or eliminate peripheral heating of the 'oven' are described in U.S. Pat. No. 3,169,389 (Green et al.), U.S. Pat. No. 3,232,093 (Burow et al.), U.S. Pat. No. 5,005,399 (Holtzclaw et al.), and U.S. Pat. No. 5,808,178 (Rounbehler et al.). Each of these patents describe methods for directly wrapping or cladding the chromatographic column with a resistive heating element. Methods are also described for positioning the resulting metal clad column adjacent to a cooling source to decrease cooling times. This method of heating can be difficult to implement in practice because of uneven heating of the column due to local hot or cold spots in the resistive heating element surrounding the column or in the environment around the heating element. Uneven heating of the column in turn compromises the quality of the analysis.

Alternative methods for heating chromatographic columns by means of microwave heating are described in U.S. Pat. No. 4,204,423 (Jordan) and U.S. Pat. No. 5,808,178 (Rounbehler et al.). Potential advantages of microwave heating are selectivity, efficiency and speed. Suitable objects placed in a microwave oven will be heated when the oven is operated, but the oven itself will not be heated. Microwave heating occurs in materials which absorb microwave energy and convert it into heat. Thus, chromatographic columns or column assembles which contain appropriate microwave absorbing materials will be selectively heated in a microwave oven while leaving the oven itself cool. Selective microwave heating makes possible more efficient heating because most thermal energy is transferred directly to the object to be heated. As compared to existing GC ovens, faster heating and cooling is also possible with microwave heating because less material is heated.

In order to heat a material in a microwave oven, the material must absorb microwave energy at least in part. Standard GC capillary columns are made of fused silica and polyimide. Neither of these materials absorb microwave energy appreciably. Consequently, these columns cannot be heated in a microwave oven in the manner taught by Jordan. The Applicant's co-pending U.S. patent application Ser. No. 09/108,297, entitled "Chromatography Column For Microwave Heating", addresses this limitation. It describes the design of chromatographic columns incorporating microwave absorbing material facilitating microwave heating.

There is another fundamental limitation in the method taught by Jordan. He does not describe any specific oven design in which a chromatographic column can be heated in a useful manner. To function properly, a GC column must not only be heated, it must be heated precisely. The temperature profile along the length of the column must be controlled within tight tolerances. For most applications in existing chromatographic ovens, the column temperature is kept essentially constant except for the ends which are usually maintained at a higher temperature. For other applications, it is useful to have a different temperature profile along the length of a column, such as a linear profile or a periodically varying profile.

Common capillary gas chromatographic columns range in size from 0.1 to 0.53 mm in internal diameter and from 4 to 60 meters in length. It is clearly impractical to build a microwave oven which heats a 60 meter column stretched out lengthwise. To get such a long chromatographic column into a practically sized oven, the column must be put into a more compact form. Chromatographic columns are usually quite flexible, especially fused silica capillary columns. Consequently, these columns can readily be coiled up into compact circular bundles having diameters as small as several centimeters (though other bundle shapes with appropriate bend radii can also be made). In bundled form, a chromatographic column can be heated within a microwave oven of practical size so that a desired temperature profile is achieved along the length of the column To achieve a desired temperature profile along the length of a coiled GC column with microwave heating, the microwave heating apparatus must be specifically designed to expose the coiled column to a specific electromagnetic field gradient along the column length. This is only achievable with a properly designed microwave heating apparatus and not with a generic microwave oven. Jordan does not describe how to design a microwave heating apparatus in which the electromagnetic field distribution is controlled in such a manner that a GC column is heated to a desired temperature profile.

Most gas chromatographs heat chromatographic columns isothermally (except for the ends) at a given time; i.e. the temperature of the entire column is kept at the same value at a given time though the specific isothermal temperature may change over time. The term "profile" is used herein to refer to the temperature versus position along the length of the column at a fixed point in time, as opposed to the temperature of the column as a function of time.

To isothermally heat a chromatographic column having a fixed microwave loss factor along its length in a microwave oven requires that the column must be exposed to the same electromagnetic field strength over its entire length (except for the ends which can be heated by the injector and detector assemblies) such that the whole of the column absorbs equal thermal energy and thus remains at the same temperature. Obtaining the desired temperature profile requires precise control of the electromagnetic field strength within the microwave oven. This cannot be achieved with conventional box-like, rectilinear, multi-mode microwave ovens where the electromagnetic field varies in an extremely complex manner throughout the oven volume. It can only be achieved with a microwave oven specifically designed to heat a chromatographic column.

3. Solution to the Problem

There are three essential features of a useful microwave oven to be used for heating coiled chromatographic columns: (1) The oven must be a single mode oven within which the electromagnetic field is predictable; (2) The electromagnetic field within the oven must have smoothly varying, continuous isofield lines oriented about a central axis such that individual coils of the column bundle can physically trace a path along or around the isofield lines resulting in a desired temperature gradient in each column coil; and (3) The electromagnetic field strength must vary from one coil to the next in the bundle by an increment sufficient to achieve the desired temperature gradient from one coil to the next.

The simplest column bundle geometry is that of a circular helix wherein each column coil is lined up adjacent to the next such that the overall bundle shape is that of a thin walled, constant diameter cylinder. To heat such a column bundle isothermally assuming the microwave absorption characteristics of the bundle do not significantly vary along the length of the column, the electromagnetic field strength must be equal (or nearly so) at all points in the cylindrical surface formed by the coiled column. Therefore, the electromagnetic field must be radially symmetric (rotationally invariant) and axially invariant. A microwave oven capable of generating such a field must itself be radially symmetric, i.e., circular in cross-section. Axially, it must be constructed to establish an equal electromagnetic field strength along in the length of the column bundle.

The present invention describes a number of chromatographic column microwave oven embodiments which can be used for heating chromatographic columns. Most such embodiments are radially symmetric in construction. Embodiments include coaxial transmission line ovens, coaxial resonant cavity ovens, and circular cylindrical resonant cavity ovens. A preferred embodiment of the oven is single mode resonant cavity and specifically a $TM_{010}$ cylindrical resonant cavity. This cavity can be tuned to deliver virtually all available microwave power to the column heating element by adjusting the length of the coupling antenna.

If constructed in an axially invariant manner, all of these oven structures will typically have an electromagnetic field that varies in the axial direction. The $TM_{010}$ cylindrical resonant cavity oven has the least variation. Several methods are described to alter the axial field distribution to which a chromatographic column bundle is exposed in a microwave oven so that a desired chromatographic column temperature profile is obtained. These methods include: (1) axially varying the geometry of the metal wall of the microwave oven; (2) axially varying the geometry of the inner conductor or central antenna; (3) axially varying the thickness of a dielectric insert in the oven; (4) axially varying the geometry of the coiled column or column heating element in the oven; or (5) axially varying the electromagnetic loss factor of the column heating element. In addition to these methods, a thermally conductive material can be used in the chromatographic column assembly to help eliminate any unwanted temperature variability that may exist.

There are two additional problems to be addressed in a useful chromatographic column microwave oven. The first concerns unwanted heat transfer from the column by air in the oven. The second concerns prevention of cold spots in the column ends where they are taken from the oven and connected to the injector and detector assemblies of the gas chromatograph. Methods are described herein for solving both problems such that the temperature profile of a column heated in a microwave oven is similar to that in conventional resistively-heated chromatographic ovens. In addition, methods are described for establishing useful column temperature profiles other than the conventional isothermal profile.

SUMMARY OF THE INVENTION

The present invention provides a single mode microwave oven for heating coiled chromatographic columns to a desired temperature profile. The oven can specifically be used to obtain an essentially isothermal profile, a linear temperature profile, or a periodically-varying temperature profile. To achieve a specific column temperature profile, the chromatographic column microwave oven establishes: (1) an electromagnetic field characterized by smoothly varying, continuous isofield lines oriented about a central axis such that individual column coils of a column bundle can physically trace a path along or around the isofield lines resulting in a desired temperature profile in each column coil; and (2) a controlled electromagnetic field gradient from one coil of the column bundle to the next so the desired temperature gradient is established from one coil to the next and thus along the whole of the column. Oven design variations include coaxial transmission line structures, coaxial resonators, and cylindrical resonators. A preferred oven design uses a cylindrical resonant cavity structure which is tuned to deliver the maximum amount of available microwave energy into the cavity. Each oven design may require a means of controlling the electromagnetic field gradient in the axial dimension of the oven. All such means involve varying the oven characteristics in the axial direction and include: (1) varying the geometry of the metal wall of the oven; (2) varying the geometry of the center conductor or antenna; (3) varying the thickness of a dielectric insert; (4) varying the geometry of the column heating element; and (5) varying the loss factor of the column heating element. These methods can be augmented with thermally conductive, electrically insulating material in the chromatographic column assembly to better distribute thermal energy. For best operation, vacuum conditions should be established within the oven during the heating process to prevent undesired heat flow from and along the column by air moving in the oven. Cooling of the column can best be achieved by reducing the microwave energy supplied to the heating element and reintroducing air into the oven.

It is the object of the invention to provide a chromatographic column microwave oven capable of faster heating and cooling rates than with conventional column ovens.

It is the object of the invention to provide a chromatographic column microwave oven for which it is possible to maximize the efficiency of power delivery to the column.

It is the object of the invention to provide an extremely small chromatographic column oven.

It is the object of the invention to provide a chromatographic column microwave oven capable of establishing a controlled temperature profile along the column length.

It is the object of the invention to provide a chromatographic column microwave oven that is radially symmetric in constriction.

It is the object of the invention to provide a chromatographic column microwave oven in which the axial construction of the oven is varied to control the axial electromagnetic field gradient in the oven.

It is the object of the invention to provide a chromatographic column microwave oven that can establish a periodically-varying column temperature profile.

It is the object of the invention to provide a chromatographic column microwave oven in which cold spots are prevented at the column ends.

BRIEF DESCRIPTION OF THE DRAWINGS

The present invention can be more readily understood in conjunction with the accompanying drawings, in which:

FIGS. 9 and 10 are graphs showing the radial electric field and resultant microwave power distributions respectively for the $TM_{010}$ mode in a cylindrical resonant cavity.

DETAILED DESCRIPTION OF THE INVENTION

Figure 1:
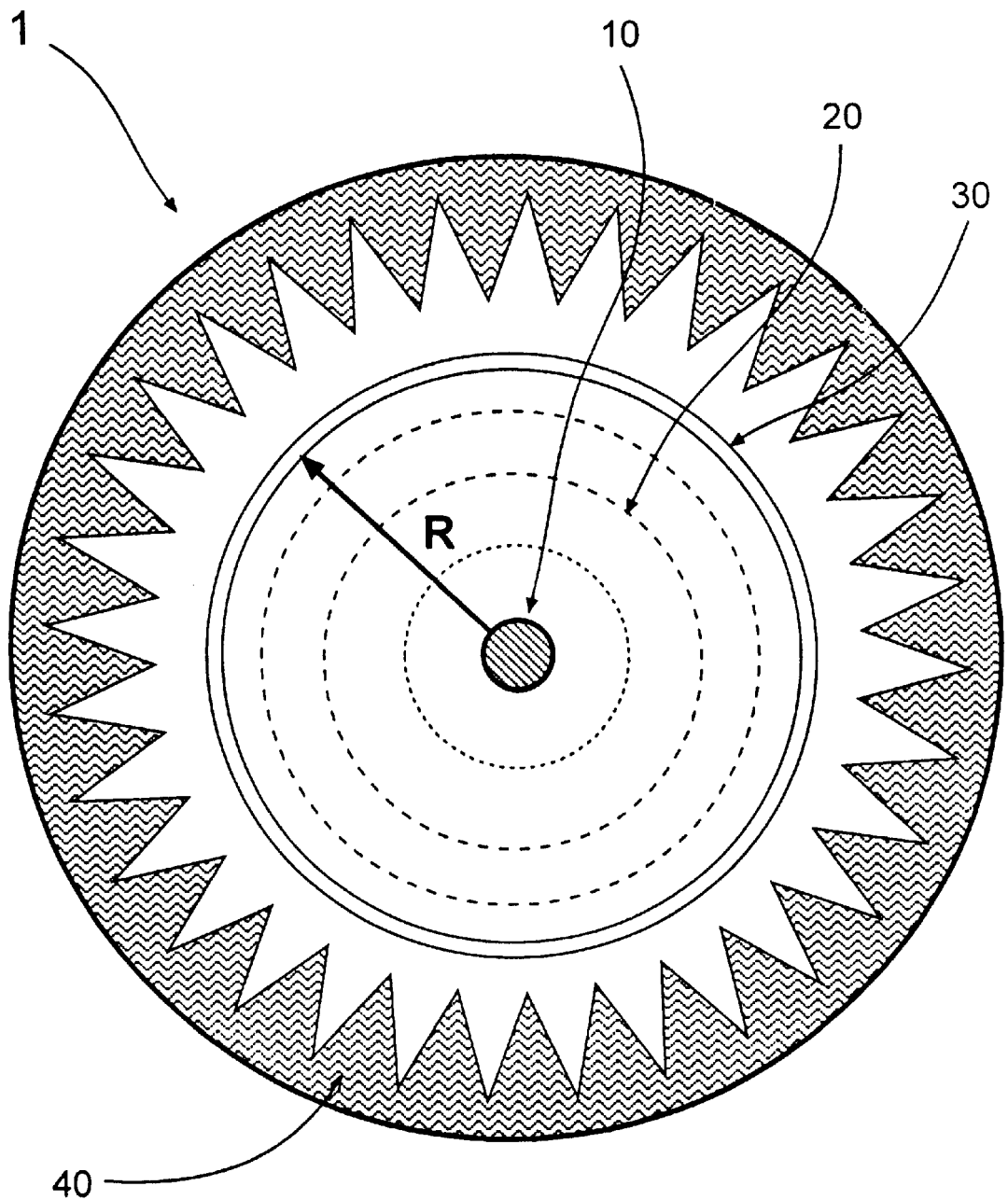
FIG. 1 is a cross-sectional view of a spherical chromatographic column microwave oven in which the chromatographic column is exposed to a constant field strength over its entire length.

Potential advantages to be derived from heating chromatographic columns in microwave ovens are heating selectivity, efficiency, and speed. Suitable objects placed in a microwave oven will be heated when the oven is operated, but the oven itself will not be heated. In the descriptions of microwave ovens for chromatographic column described herein, the term "microwave" is used broadly to refer to electromagnetic radiation in the frequency range from 10 MHz to 100 GHz.

Microwave heating occurs in materials that absorb microwave energy and convert it into heat. Thus, chromatographic columns or column assembles which contain appropriate microwave absorbing materials will be selectively heated in a microwave oven while leaving the oven itself cool. Selective microwave heating makes possible more efficient heating because most thermal energy is transferred directly to the object to be heated. In addition, faster heating and cooling is possible because much less material is heated.

Conventional microwave ovens are typically closed metal boxes of at least a cubic foot in volume within which the electromagnetic energy is confined. They operate at 2.45 GHz at which the wavelength of electromagnetic waves is about 4.82 inches. A conventional microwave oven acts as a multi-mode resonant cavity. A resonant cavity is a structure within which the interference pattern between multiply reflecting electromagnetic waves excited in the cavity resolves itself into a well defined and stable standing wave pattern. A multi-mode resonant cavity is one in which many different and unique standing wave patterns can exist. A conventional microwave oven can support a very large number of modes because the internal dimensions of the oven are many times the wavelength. The result is a complex, intermingled pattern of overlapping standing wave patterns from different resonant modes. At some points the electromagnetic field strength is high and at other points the field strength is zero. Objects heated in such complex electromagnetic fields are heated in similarly complex and uneven patterns. The spacing between adjacent hot spots is typically less than one wavelength. Manufacturers of such ovens attempt to smooth out the temperature distributions of materials heated in the ovens with: (1) mode stirrers (e.g., metal fans) to stir the mode pattern in the oven; and (2) rotating platforms to physically move material around in the oven while it heats. These methods provide only modest improvements in the electromagnetic field profile to which material is exposed in conventional microwave ovens.

Most gas chromatographs heat chromatographic columns isothermally, except for the ends which are kept hotter by the injector and detector assemblies (i.e., the temperature of the central length of the column is kept at the same value). To isothermally heat a chromatographic column having a constant loss factor along its length in a microwave oven requires that the column must be exposed to the same electromagnetic field strength over its entire length, such that the whole of the column absorbs equal thermal energy and is thus kept at isothermal conditions.

The most common type of chromatographic column used in gas chromatographs is the fused silica capillary column. These columns typically range in size from 0.1 to 0.53 mm in internal diameter and from 4 to 60 meters in length. Most chromatographic columns are quite flexible, especially fused silica capillary columns. Consequently, these columns can readily be coiled up into compact circular bundles having diameters as small as several centimeters (though other bundle shapes with appropriate bend radii can also be made). Even with such a small column bundle, a conventional consumer microwave oven cannot be used to heat the column bundle isothermally. Even a bundle as small as two centimeters in diameter would be exposed to an electromagnetic field gradient so large as to produce great variation in temperature along the column length.

A more fundamental flaw with conventional microwave ovens is that they are box-like. Box-like resonant cavities tend to generate field distributions symmetrical in rectangular coordinates. Constant field strength contour lines (which herein will be called isofield lines) thus tend to be rectilinear. Existing chromatographic columns cannot be bent into tight rectangular shapes, however, so they cannot be made to trace the rectilinear isofield lines, making isothermal heating impossible. Consequently, non-rectangular oven geometries are preferred with currently available chromatographic columns.

An Oven Utilizing Free Space Propagation

FIG. 1 shows the cross section of a spherical chromatographic microwave oven 1 that could be used. A point source antenna 10 emits electromagnetic waves 20 which propagate spherically outward from the antenna 10. This is free space propagation. At the surface of any sphere a fixed distance from the point source antenna 10, the electromagnetic field strength is constant.

A chromatographic column 30 is coiled in such a manner that the whole length of the column is located an equal distance R from the source 10. The column 30 will absorb some portion of the energy in the electromagnetic field. The microwave energy that the column 30 does not absorb will continue to propagate outwards. To prevent unwanted reflection of the remaining electromagnetic waves back toward the column and the consequent disturbance of the isofield conditions which exist at R, an spherical absorber 40 encloses and isolates the oven. The absorber 40 absorbs microwave energy. The absorber 40 also prevents disturbance of the internal field by radiation from external sources.

The chromatographic microwave oven 1 is a poor design for several reasons. It is quite large and mechanically clumsy. It is also energy inefficient. Most of the microwave energy is absorbed by the absorber 40 and not by the column 30. This inefficiency compromises heating and cooling times and potentially increases the cost of the oven 1 because the lost microwave energy is expensive to generate. If the absorber 40 is substituted by a hollow metal sphere that internally reflects all electromagnetic energy, the oven 1 is a spherical resonant cavity. This structure is more energy efficient, but spherical resonators are not practical to use for this application.

Useful chromatographic column microwave ovens must generate stable and predictable electromagnetic field profiles having isofield lines that can be traced by a column. A chromatographic column with a constant microwave loss factor along its length that lies on an isofield line in a microwave oven will be heated isothermally in that oven. Long chromatographic columns can be reduced to a manageable size by winding them into a circular bundle. Microwave ovens with circular cross sections can be designed with radially symmetric electromagnetic fields having circular isofield lines. Because of this feature, most chromatographic column microwave ovens described herein have circular cross sections.

A typical coiled chromatographic column must be wound into more than one coil. A 60 m, 0.35 mm column wound to a diameter of 15 cm must be wound over 127 times. If bundled into a cylindrical coil of constant radius that is only one column thick, the resulting column cylinder is 4.45 cm long. The axial length of the coil is of the same order of magnitude as its diameter. Thus, the axial electromagnetic field distribution is as important in a chromatographic column microwave oven as the radial field distribution. Suitably designed microwave ovens having circular cross-sections combine: (1) radially symmetric electromagnetic field distributions; and (2) well defined axial electromagnetic field gradients.

Coaxial Chromatographic Column Microwave Ovens

Figure 2:
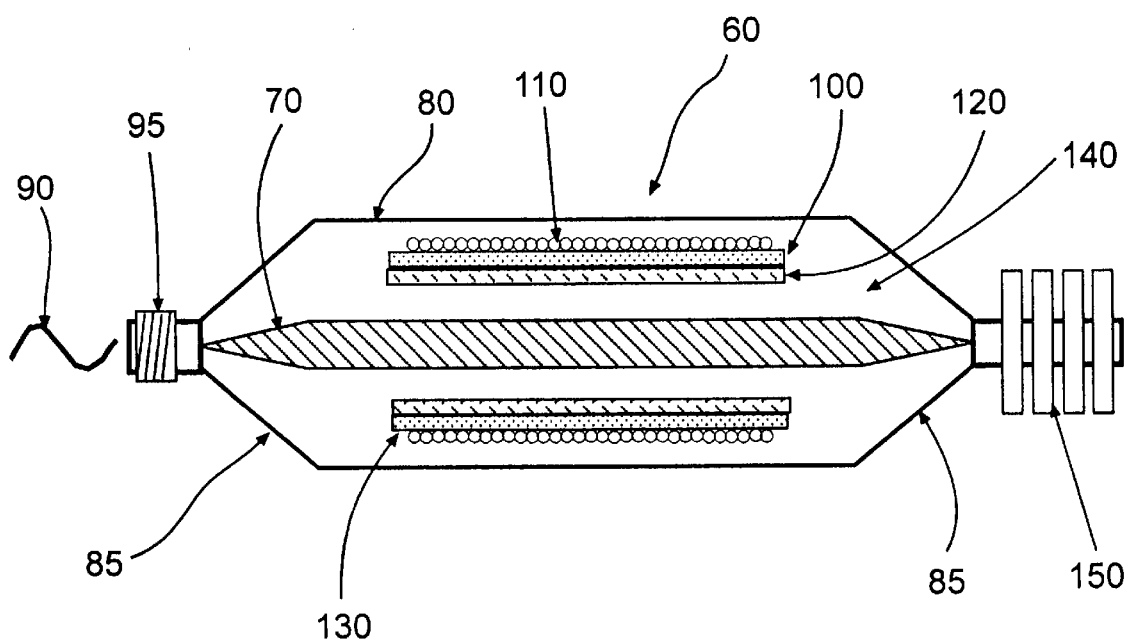
FIGS. 2 and 3 are two orthogonal cross-sectional views of a chromatographic column microwave oven wherein the oven is a coaxial transmission line.
Figure 3:
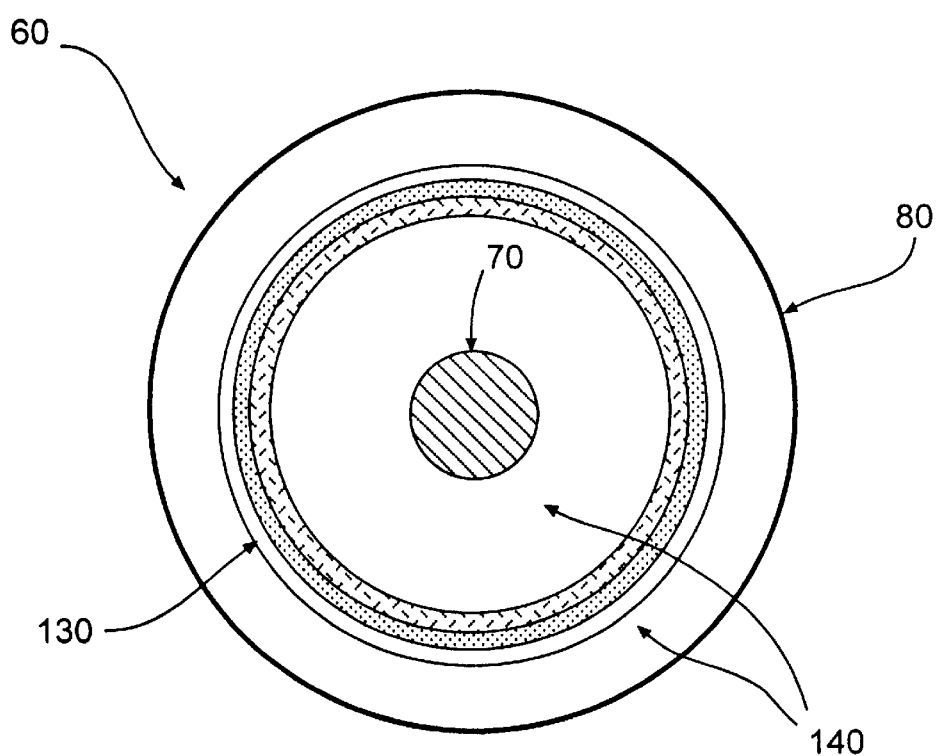

FIGS. 2 and 3 show two orthogonal cross-sectional views of one embodiment of a cylindrically shaped chromatographic microwave oven 60. The oven 60 is a coaxial transmission line structure. It is the coaxial analog of the spherical oven 1. FIG. 2 shows a cross sectional view along the central axis of the chromatographic microwave oven 60. FIG. 3 shows the radial cross section perpendicular to the central axis in the middle of the oven 60.

A microwave signal 90 is coupled into the oven 60 through a coaxial connector 95. The electromagnetic field propagates from left two right in the space 140 between a metallic cylindrical inner conductor 70 of the coaxial oven 60 and a metallic cylindrical outer wall 80. To prevent undesirable reflection of microwave energy out of the microwave oven 60 through the connector 95, a conical impedance matching section 85 is used to transition between the smaller-diameter coaxial connector 95 and the larger-diameter main section of the coaxial oven 60.

The outer enclosure of oven 60 consisting of conical impedance matching section 85 and outer wall 80 defines the boundary of a cavity which substantially prevents electromagnetic radiation from escaping from the oven 60. All of the chromatographic microwave ovens described herein comprise cavities which substantially isolate electromagnetic phenomenon within the interior space defined by the boundaries of the cavity from the environment.

A cylindrical sheet of microwave absorbing material 100 is positioned concentrically about the central axis of the oven 60 in the gap between the inner and outer conductors 70 and 80. Around and adjacent to absorbing material 100 is coiled a chromatographic column 110 which is heated together with the absorbing material 100 in the oven 60. Together, the absorbing material 100 and the adjacent column 110 constitute a microwave absorbing chromatographic column assembly as taught, for example, in the Applicant's co-pending U.S. patent application Ser. No. 09/108,297, entitled "Chromatography Column For Microwave Heating", which is incorporated herein by reference. It should be understood that absorbing material 100 and the column 110 could be substituted with any microwave absorbing column assembly without materially affecting the teaching of this invention.

An optional mechanical support 120 is provided to hold the absorbing material 100 and the column 110 in place within the oven 60. As shown, the mechanical support 120 is a thin walled cylindrical structure of fixed length outside of which is wrapped the absorbing material 100 and the column 110. The mechanical support 120 need not be a cylindrical pipe nor must the absorbing material 100 and the column 110 be wrapped around it. It could just as readily be place between absorbing material 100 and the column 110 or it could lie outside of both without materially affecting the performance of the oven 60.

Taken together, the absorbing material 100, the column 120, and the mechanical support 130 constitute a common element in all chromatographic column microwave oven embodiments described herein. Henceforth, they are treated as a single element 130 and called a column heating element. The term column heating element incorporates any microwave absorbing column assembly together with an optional mechanical support. Many different embodiments and configurations of the these subcomponents are possible. It should obvious be one of average skill in the art that the invention is not limited to a specific one.

Microwave energy not absorbed by the column heating element 130 passes though a second impedance matching transition 85 and into a load element 150 which absorbs it.

All cylindrical elements within the oven 60 are concentrically oriented about the same axis. Consequently, the electromagnetic field is radially symmetric in the oven 60. The diameter of the oven 60 built in accordance with this specification is typically between 3 and 25 cm.

As specified, the oven 60 has significant drawbacks. First, the electromagnetic field strength is not constant axially in the oven 60 nor in the column heating element 130. The electromagnetic field strength decreases axially as it propagates through the oven 60 because energy is absorbed by the column heating element 130. Thus, there is a temperature gradient from high to low along the length of the column 110 in the direction of microwave propagation There are several ways to adjust the axial variation in field strength. They are described subsequently. The second weakness of the oven 60 is that it is energy inefficient. Much of the microwave energy 90 injected into the oven 60 is lost in the load 150. It does not heat the column heating element 130. The loss factor of the column heating element 130 can be increased so that a higher percentage of the microwave energy 90 is dissipated in the column heating element 130. However, this increases the gradient of the electromagnetic field in the axial direction making steeper the temperature profile of the column 110.

A coaxial resonant cavity chromatographic column microwave oven is far more energy efficient than the coaxial transmission line microwave oven 60. Resonant cavities are a special class of cavity as the term is used herein in which confined electromagnetic energy can develop into high field strength standing wave patterns as a result of multiple internal reflection. Virtually all microwave energy injected into a resonant cavity chromatographic column microwave oven will be absorbed by the column heating element. Coaxial resonant cavities have radially symmetric electric fields just as coaxial transmission lines do.

Figure 4:
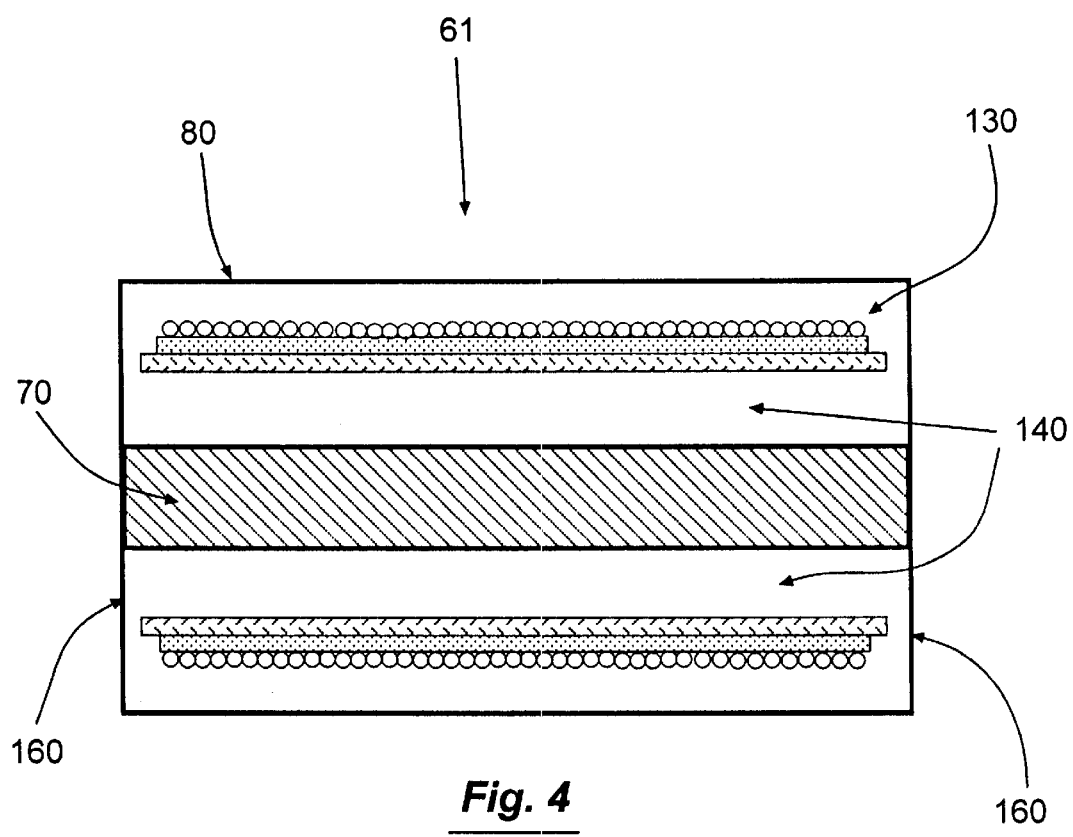
FIG. 4 is a cross-sectional view along the central axis of a chromatographic column microwave oven wherein the oven is an short-circuited coaxial resonant cavity.

FIG. 4 illustrates a chromatographic column microwave oven 61 constructed as a short circuited coaxial resonant cavity. FIG. 4 shows the cross section of the oven 61 along its central axis. The radial cross section of the oven 61 is identical to that of the oven 60 shown in FIG. 3. A metallic inner conductor 70 and a concentric metallic outer conductor 80 comprise the coaxial parts of the oven 61. They are electrically connected together at both ends with round metal discs 160 which also serve to seal the oven 61 if air in the space 140 is pumped out. A cylindrical column heating element 130 is centered around the central axis.

The internal axial length of the oven 61 is 'D'. The oven 61 will resonate at those frequencies at which the wavelength is equal to 2D, D, 2D/3, D/2, 2D/5 . . . and so on. At the lowest order resonance, the cavity is one half a wavelength long. Ignoring the absorption of the field by the column heating element 130, the axial electric field strength at a fixed radius within the oven 61 is given by the following equation:

$$E(z)=E_{max} \sin(\pi z) \qquad (1)$$

where:

z is the normalized axial position in the oven 61 (i.e., z=0 at one end cap 160 and z=1 at the other), E(z) is the axial electric field strength in the oven, and $E_{max}$ is the maximum axial electric field strength.

Figure 5:
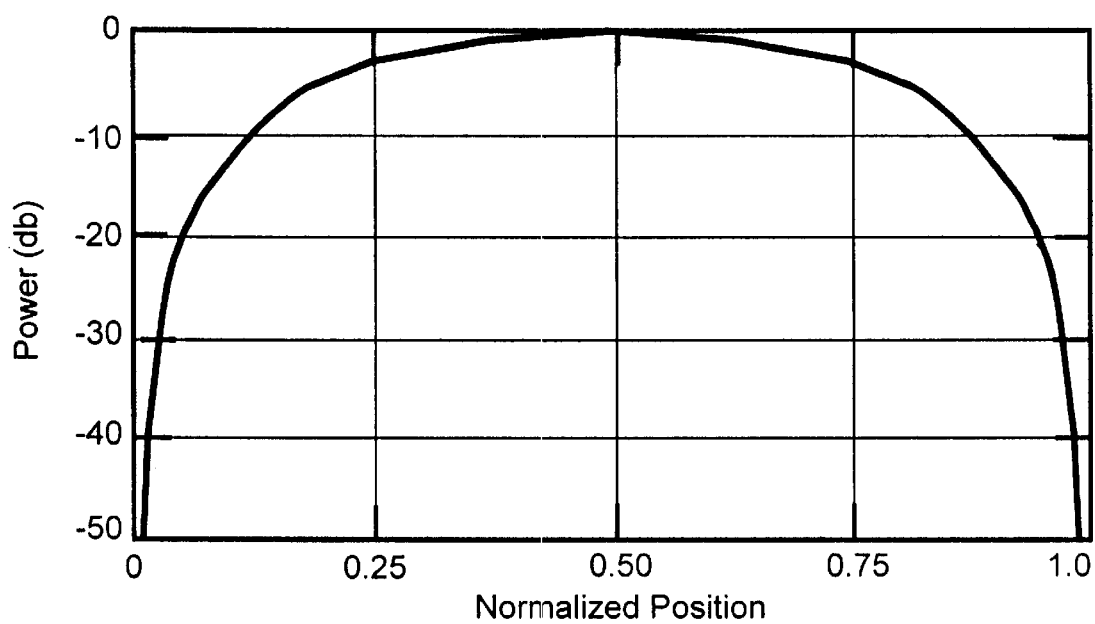
FIG. 5 is a graph showing the microwave power distribution along the length of a short-circuited coaxial resonant cavity.

The axial power distribution of the electric field is described by the following equation:

$$P=20 \log 10[E(z)/E_{max}] \qquad (2)$$

where P is the power in decibels (dB) relative to the maximum power point. FIG. 5 is a graph showing the electric field power distribution in an oven 61 along its length.

Figure 6:
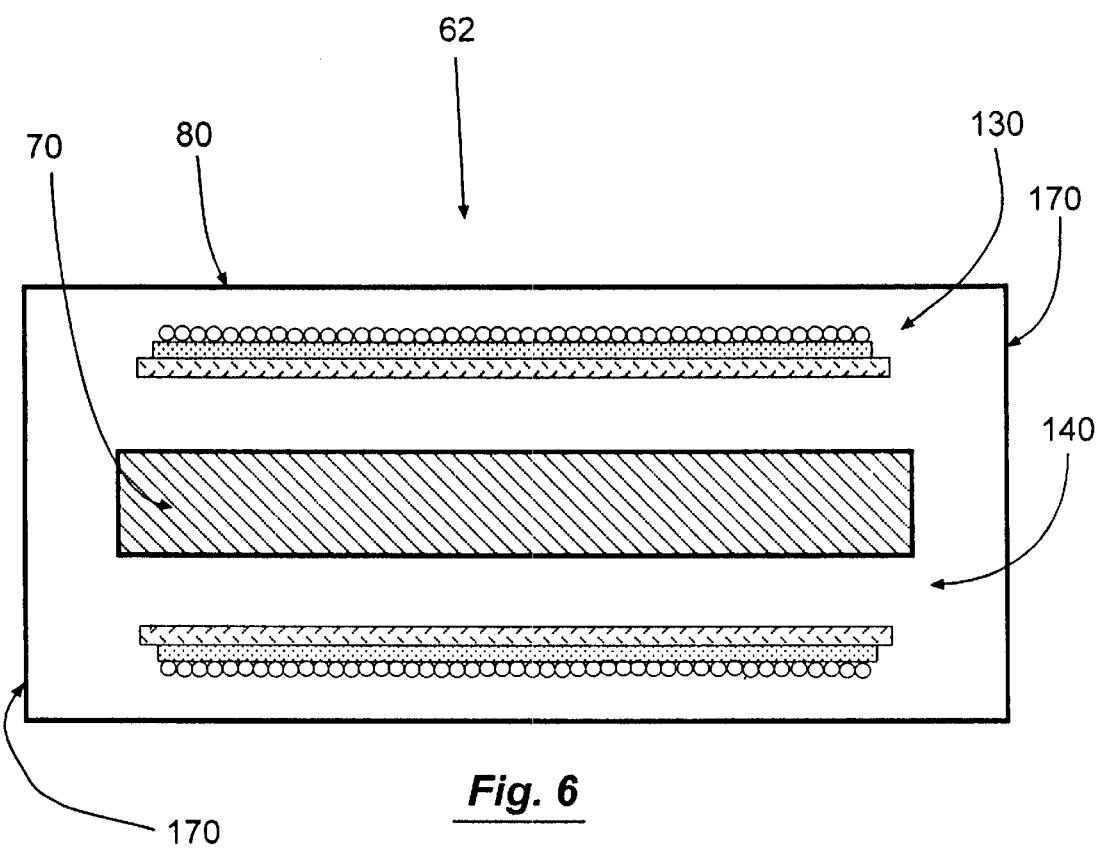
FIG. 6 is a cross-sectional view along the central axis of a chromatographic column microwave oven wherein the oven is an open-circuited coaxial resonant cavity.

FIG. 6 illustrates a similar chromatographic column microwave oven 62 constructed as an open circuited coaxial resonant cavity. FIG. 6 shows the cross section of the oven 62 along its central axis. The radial cross section of the oven 62 is identical to that of the oven 60 as shown in FIG. 3. The oven 62 has a metal cylindrical inner conductor 70, and concentric metal cylindrical outer conductor 80, between which is a concentric cylindrical oven heating element 130. The inner conductor 70 and the outer conductor 80 are not connected together electrically. The oven ends are sealed with circular endplates 170 such that the air in the space 140 inside the oven 62 can be pumped out. The endplates 170 can be metallic or nonmetallic. If metallic, then the outer conductor 80 must be longer than and not come into electrical contact with the inner conductor 70 as shown in FIG. 6.

The length of the inner conductor 70 is 'D'. The oven 62 will resonate at those frequencies at which the wavelength is equal to 2D, D, 2D/3, D/2, 2D/5 . . . and so on. At the lowest order resonance, the inner conductor 70 is one half a wavelength long. Ignoring the absorption of the field by the column heating element 130, the axial electric field strength at a fixed radius within the oven 62 is given by the following equation:

$$E(z)=E_{max} \cos(\pi z) \qquad (3)$$

Figure 7:
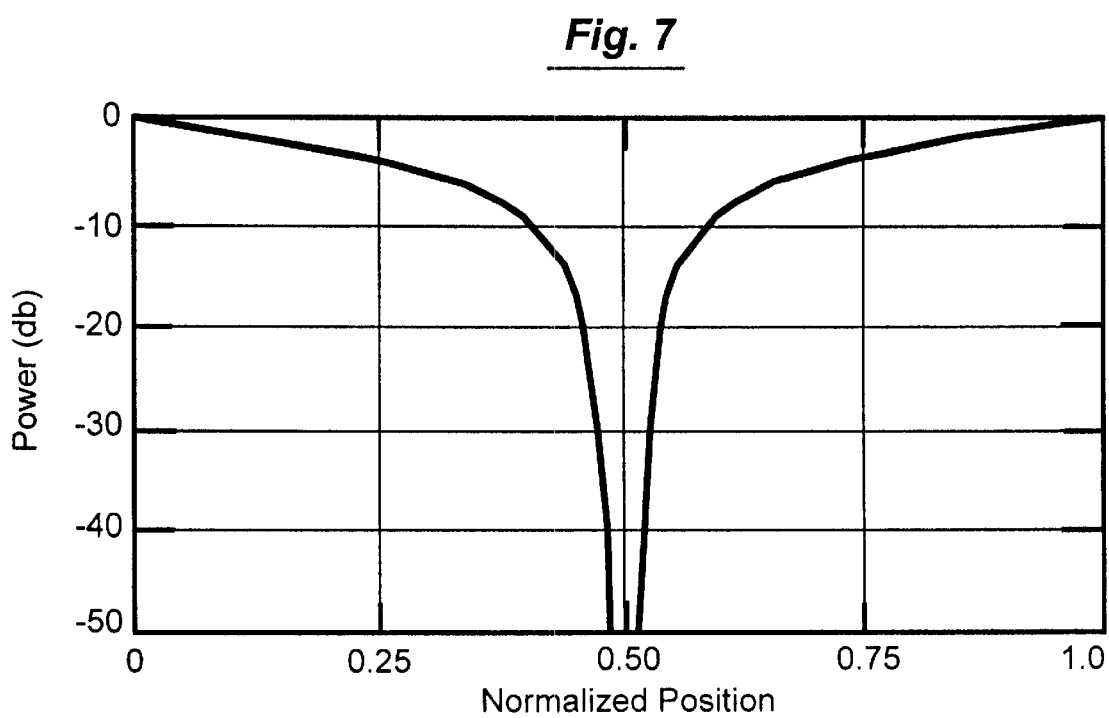
FIG. 7 is a graph showing the microwave power distribution along the length of an open-circuited coaxial resonant cavity.

FIG. 7 is a graph showing the corresponding power distribution of the oven 62 along the length of the center conductor 70.

Within the ovens 61 and 62, each single coil of the chromatographic column follows an isofield line and is thus heated isothermally. However, the axial power distributions of the electric fields in the ovens 61 and 62 respectively vary greatly as shown in FIG. 5 and 7 respectively. The power varies by 50% (about 3 dB) over the center 50% of the oven 61. The corresponding temperature gradient would also be approximately 50% as compared to ambient temperature.

There are methods, which will be described subsequently, with which the axial power distribution of the electromagnetic field can be altered in the ovens 61 and 62. But, the axial field strength cannot be made constant over the entire oven length. Consequently, the ovens 61 and 62 would be much longer physically than the column heating element 130. The absorption of microwave energy by the column heating element 130 in the ovens 61 and 62 will somewhat alter the power distributions shown in FIG. 5 and 7 without significantly altering the essential characteristics of these oven embodiments.

Another type of coaxial resonant cavity that could be used is a hybrid of those used the ovens 61 and 62 (i.e., a cavity with a short circuit on one side and an open circuit on the other). This cavity would resonate at frequencies where the wavelength is equal to 4D, 4D/3, 4D/5, 4D/7 . . . and so on, where D is equal to the length of the center conductor.

Operating Chromatographic Column Microwave Ovens in Vacuum

A problem common to the chromatographic column microwave ovens 60, 61, and 62 and all other oven embodiments described herein is redistribution of heat in the column heating element 130 by air. If gap 140 is filled with air at atmospheric conditions, some of the heat in column heating element 130 will be transferred to the air. Because hot air rises, air movement alters the heat distribution in the oven. Over time, the upper part of the ovens including the upper part of column heating element 130 becomes hoffer than the lower parts. This undermines the isothermal conditions that a carefully designed and symmetrical oven can establish and it will slow heating and cooling times. This problem can be partially addressed by altering the geometry of the oven to compensate for the heat transport in the air. However, this is not a good solution because air driven heat transport is unpredictable. A better solution to the problem is to pump most of the air out of the interior of the oven such that the undesirable transport of thermal energy from the column heating element 130 does not occur at a significant rate. Subsequent cooling of the column heating element 130 is achieved by reintroducing air into the oven interior and even pumping air through the oven to more quickly remove the thermal energy from the column heating element 130. Heating in vacuum maximizes heating and cooling rates. The performance of all chromatographic column microwave ovens described herein is significantly improved by operating them in vacuum conditions.

Circular Cylinder Resonant Cavities

Figure 8:
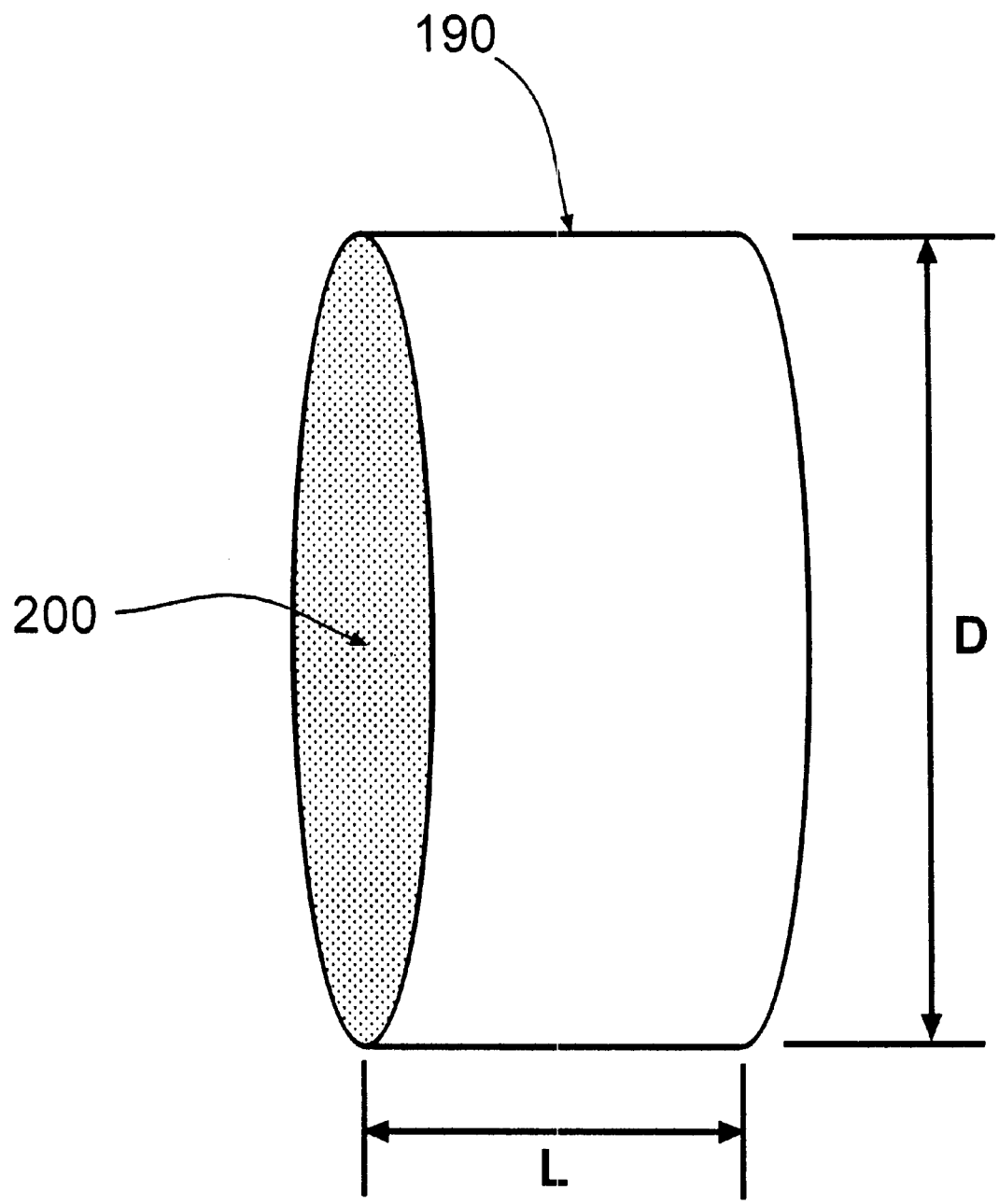
FIG. 8 is a perspective view of a cylindrical resonant cavity.

Certain modes of circular cylindrical resonant cavities have constant electromagnetic field strengths at fixed radii over their axial length and so are a better choice for a chromatographic column oven than coaxial resonator ovens. A circular cylindrical resonant cavity is essentially the same cavity shown in FIG. 4 without the center conductor. FIG. 8 is a drawing of such a resonant cavity having a diameter D and an axial length L. It consists of a cylindrical metal wall 190 with metal end caps 200 at either end oriented perpendicular to its central axis.

Circular cylindrical resonant cavities can support many modes if the wavelength is smaller than the length and/or the diameter of the cavity just as a conventional rectangular microwave cavity does. Some of the possible modes are radially symmetric. Others are not. Ideally, a chromatographic column microwave oven will only support one mode so that there is no uncertainty in the electromagnetic field distribution. If more than one mode is present, the relative power distribution between the modes can change such that the field distribution varies over time. Thus, a chromatographic column microwave oven should be a single mode oven and not a multi-mode oven.

The resonant frequencies for different modes in cylindrical resonant cavities can be calculated from cavity length L and diameter D. Table 1 shows the resonant frequency for various modes in three cylindrical resonant cavities, each with a diameter of 25 cm.

TABLE 1

| Mode | Frequency (GHz) | | |
| --- | --- | --- | --- |
| | L = 8 cm | L = 15 | L = 25 cm |
| TM010 | 0.919 | 0.919 | 0.919 |
| TE111 | 2.000 | 1.219 | 0.919 |
| TM020 | 2.108 | 2.108 | 2.108 |
| TM110 | 2.378 | 1.772 | 1.581 |
| TM011 | 2.085 | 1.354 | 1.092 |
| TE211 | 2.212 | 1.542 | 1.319 |
| TE011 | 2.379 | 1.773 | 1.582 |
| TM111 | 2.379 | 1.773 | 1.582 |
| TM210 | 1.960 | 1.960 | 1.960 |
| TE311 | 2.469 | 1.892 | 1.715 |
| TM211 | 2.712 | 2.200 | 2.049 |
| TE411 | 2.762 | 2.261 | 2.115 |

The lowest order (i.e., lowest frequency) mode in each cavity is the $TM_{010}$ mode which resonates at 0.919 GHz. As the ratio between D and L decreases, the frequency spread between the $TM_{010}$ mode and the higher order modes decreases. When D/L is one, the $TM_{010}$ and $TE_{111}$ modes resonate at the same frequency and several other modes resonate at frequencies not much higher. This is a situation to be avoided. If a chromatographic column microwave oven is made with a D:L ratio of at least 2 and preferably 3, the $TM_{010}$ mode is clearly separated from the other modes such that the oven will operate as a single mode oven.

The $TM_{010}$ mode has other attractive characteristics for a column heating application. The electromagnetic field distribution is radially symmetric. More importantly, the axial field distribution is theoretically predicted to be constant over the whole length of the cavity when no perturbations are present in the cavity. All $TM_{0n0}$ modes where n=1, 2, 3, . . . share these important properties. The electric field distribution in a $TM_{010}$ resonant cavity is given by the following equation:

$$E(z)=E_{max}J_0(R/Ro) \qquad (4)$$

where:

$J_0$ is the zero$^{th}$ order Bessel function,

R is the radius at which E(z) corresponds, and

Ro is the radius of the resonant cavity (i.e., D/2).

FIG. 9 is a graph showing the electric field distribution across the diameter of a $TM_{010}$ cavity. There is no axial variation along the length L. FIG. 10 is a graph showing the corresponding power distribution calculated by inserting Equation 4 into Equation 2.

A Single Mode $TM_{010}$ Chromatographic Column Microwave Oven

The $TM_{010}$ circular cylindrical resonant cavity is the most suitable structure for a chromatographic column microwave oven. It has a radially symmetric, axially invariant electromagnetic field distribution and higher order modes are readily inhibited.

Figure 11:
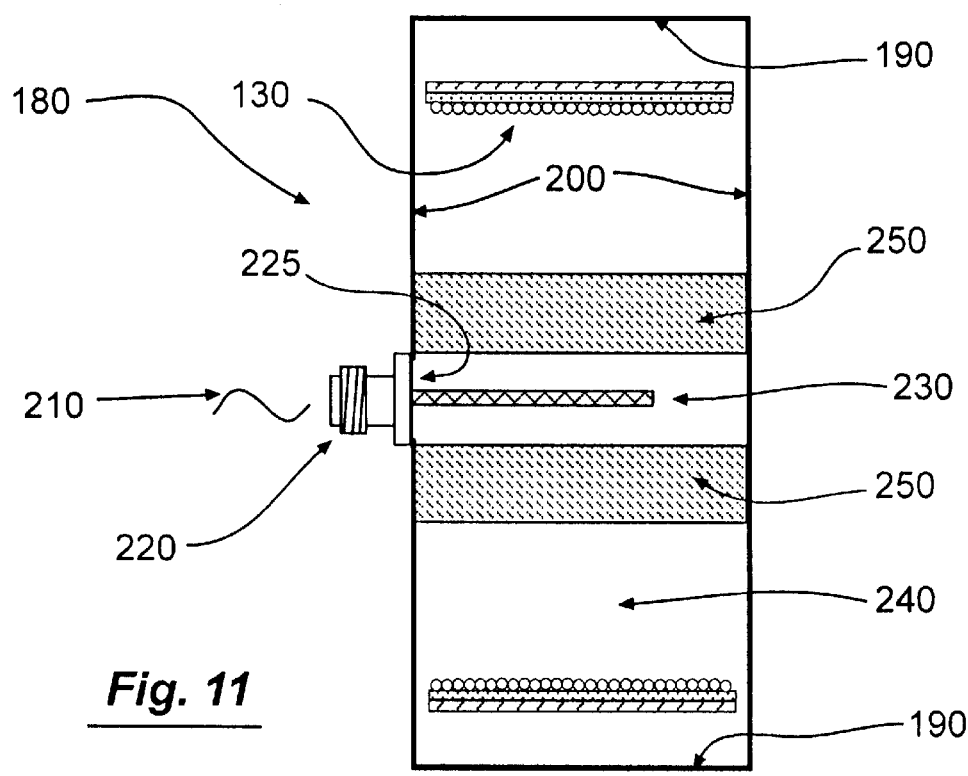
FIGS. 11 and 12 are two orthogonal cross-sectional views of a chromatographic column microwave oven wherein the oven is a cylindrical resonant cavity.
Figure 12:
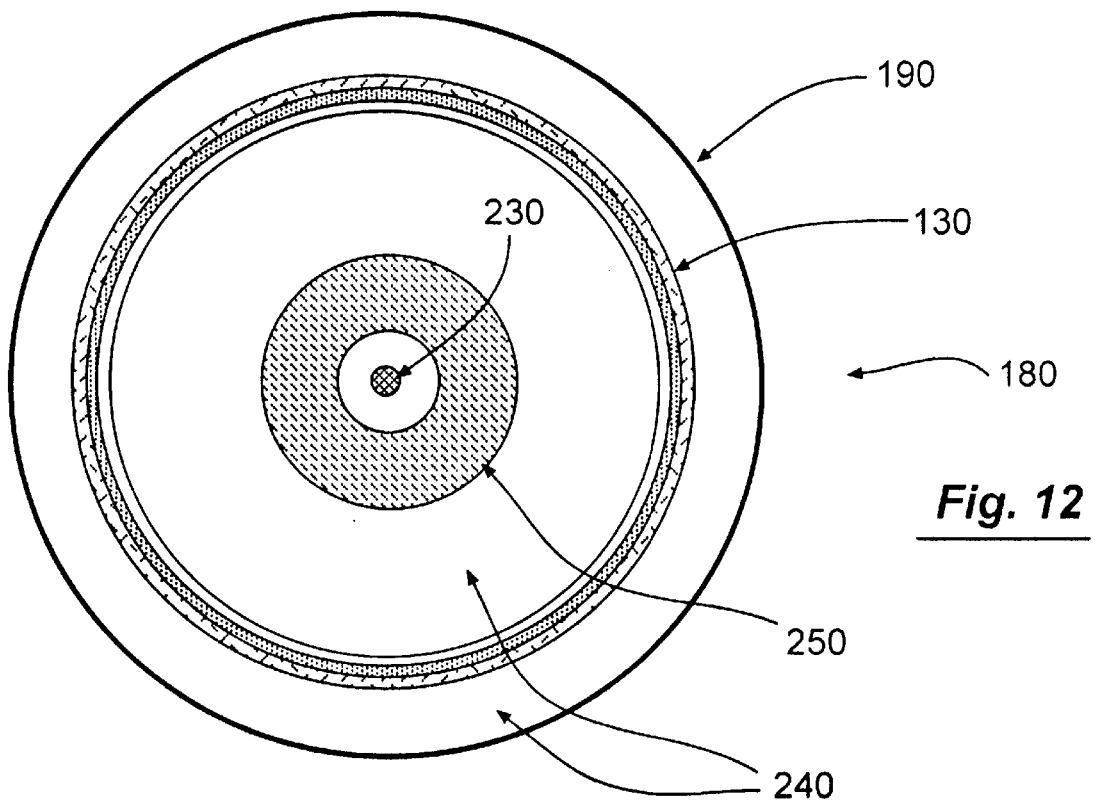

FIG. 11 and 12 show two orthogonal cross sectional views of a chromatographic column microwave oven 180 utilizing this mode. FIG. 11 is an axial view along the central axis and FIG. 12 a radial cross section. The oven 180 consists of a circular metal cylinder 190 of length L1 and diameter D1. The cylinder 190 is closed off at either end by two circular metal caps 200 of diameter D1. Together, the metal cylinder 190 and the end caps 200 form the outer wall of the chromatographic column microwave oven 180 and form a circular cylindrical resonant cavity as shown in FIG. 8. To separate the $TM_{010}$ mode from higher order modes, diameter D1 should be at least twice as great as length L1.

A hole 225 is cut in the center of one of the end caps 200. A coaxial microwave connector 220 is connected to the center of the end cap 200 with the hole 225 in it. The center conductor 230 of the coaxial connector 220 protrudes into the oven 180 along the central axis through the hole 225 in the end cap 200. The center conductor 230 must not contact end cap 200.

A microwave signal 210 transmitted through the connector 220 will radiate in part into the oven from the center conductor 230 which acts as an antenna. That portion of the microwave signal 210 not radiated into the oven 180 is reflected back out of the oven 180 through connector 220. Inside the oven 180 is a cylindrical column heating element 130 concentric with metal cylinder 190 which absorbs the microwave energy radiated into the oven 180 by antenna 230. The space 240 inside the oven 180 can be air, but preferably the air should be pumped out during the heating process.

The efficiency of the microwave oven 180 at delivering available microwave power to column heating element 130 can be maximized by tuning the oven. To achieve maximum efficiency, the oven 180 must be operated at the resonant frequency of the $TM_{010}$. In most cases, the frequency of the microwave signal will be restricted to one of two frequency bands centered at 915 and 2450 MHz respectively. These frequency bands have been set aside for such industrial usage as microwave heating. The resonant frequency of the $TM_{010}$ mode depends on the diameter of the cavity. Thus, the diameter D1 of the oven 180 must be such that the oven will resonate at the desired frequency. If a smaller diameter is needed, a cylindrical dielectric tuning element 250 can inserted into the oven 180 to cause it to resonate at a lower frequency than could be achieved otherwise with a given diameter D1. The resonant frequency of the oven 180 can be varied by adjusting the radial thickness of the dielectric 250 or by adjusting its dielectric constant. The dielectric 250 should not absorb microwave energy appreciably or it too will be heated in the oven 180, thus compromising heating and cooling times.

To further increase the efficiency of microwave power delivery, the length of the antenna 230 is adjusted to minimize the amount of microwave energy reflected from the resonant cavity (i.e. to maximize the return loss). The optimal antenna length varies with the total loss factor of the cavity which depends in turn primarily upon the loss factor of the column heating element 130. In practice, changing the length of the antenna 230 also changes the resonant frequency of the oven 180 to some extent.

When properly tuned, the chromatographic column microwave oven 180 can be over 99% efficient in delivering available microwave energy to column heating element 130 in the form of heat. Moreover, the resonant frequency of the system is generally stable over time such that the oven 180 will remain efficient once tuned.

Figure 13:
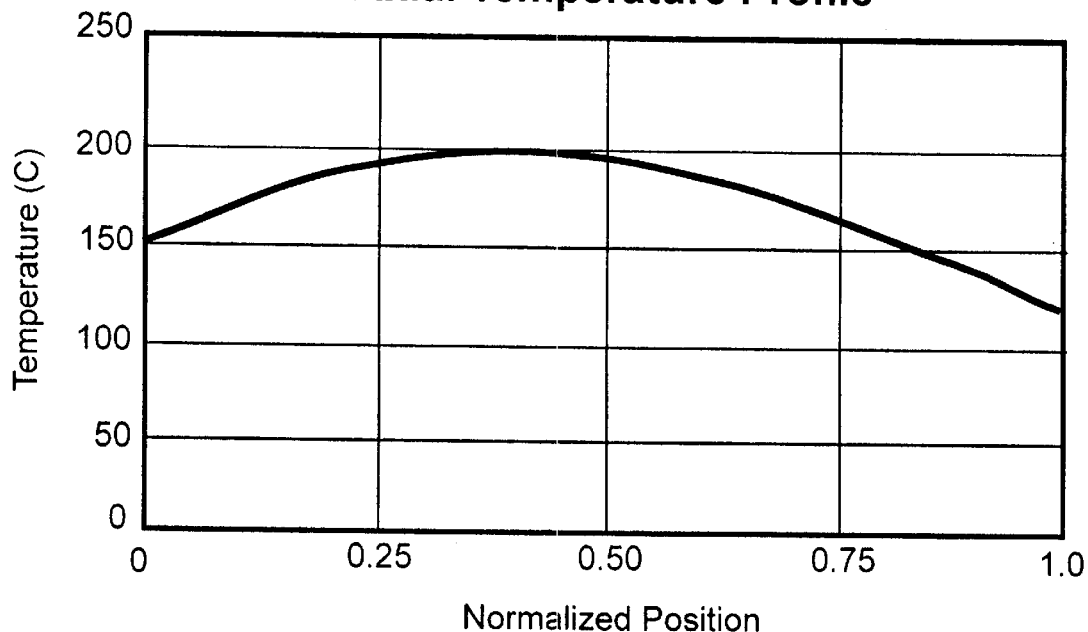
FIG. 13 is a graph showing an axial temperature distribution of a column heating element heated in the $TM_{010}$ microwave oven illustrated in FIGS. 11 and 12.
Figure 14:
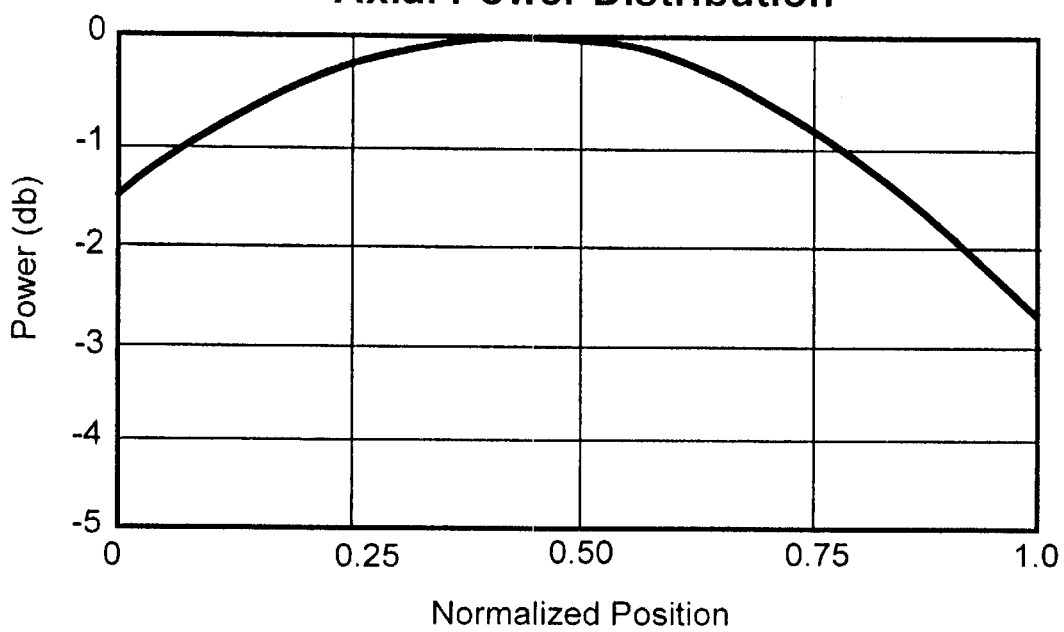
FIG. 14 is a graph showing the approximate axial microwave power distribution of the $TM_{010}$ microwave oven illustrated in FIG. 11 and 12.

A chromatographic column microwave oven 180 built as shown in FIG. 11 and 12 has a very even radial temperature profile in the column heating element 130 indicating that the electromagnetic field is radially symmetric as expected. The axial temperature profile is not typically isothermal, however, indicating that the electromagnetic field is not necessarily axially invariant in an oven 180 as would be theoretically expected. This is caused primarily by the presence of electromagnetic absorbing material in the column heating element 130 which disturbs the electromagnetic field distribution. FIG. 13 is a graph showing a typical axial temperature profile of a column heated in an oven 180. FIG. 14 is a graph showing the approximate axial power distribution giving rise to the temperature profile shown in FIG. 13. The microwave power absorbed by the column heating element 130 varies by less than 3 dB over the length of the oven 180. This is significantly better than in the previously described coaxial microwave ovens 61 and 62. Nevertheless, the temperature profile of the chromatographic column in oven 180 is not isothermal.

Modifying the Axial Field Gradient in Chromatographic Column Microwave Ovens

To achieve isothermal conditions (or at least conditions approaching isothermal conditions) on a column heating element in the various described chromatographic column microwave embodiments, the axial electromagnetic field gradient seen by the column heating element must typically be altered. There are several ways this can be achieved. The different methods will be illustrated in chromatographic column microwave ovens embodiments that are derived from the $TM_{010}$ cylindrical resonant cavity oven shown in FIGS. 11 and 12. However, these methods are as readily applied to the other ovens described herein and should be considered as general means for engineering desired axial electromagnetic field gradients into the chromatographic column microwave ovens taught in this invention.

The electric field strength decreases in strength in $TM_{010}$ resonant cavities as the radius increases toward the outer wall of the cavity as seen in Equation 4 and shown in FIG. 9 Assume R(z) represents the radius of a column heating element at each point z along it length and assume Ro(z) represents the radius of the resonant cavity at each point z along its length. If R(z)/Ro(z) is varied as a function of z, then the electric field strength E(z) will vary according to R(z)/Ro(z). Thus, controlling R(z)/Ro(z) provides a way of adjusting the axial microwave power distribution seen by a column heating element in a chromatographic column microwave oven. The electric field distribution in coaxial devices decreases from a maximum at the inner conductor to a minimum at the outer conductor just as it decreases from a maximum at the center of a $TM_{010}$ resonator to a minimum at the outer cylindrical wall. Thus, the methods described for modifying the axial electromagnetic field gradient work equally well in coaxial-based microwave ovens.

Figure 15:
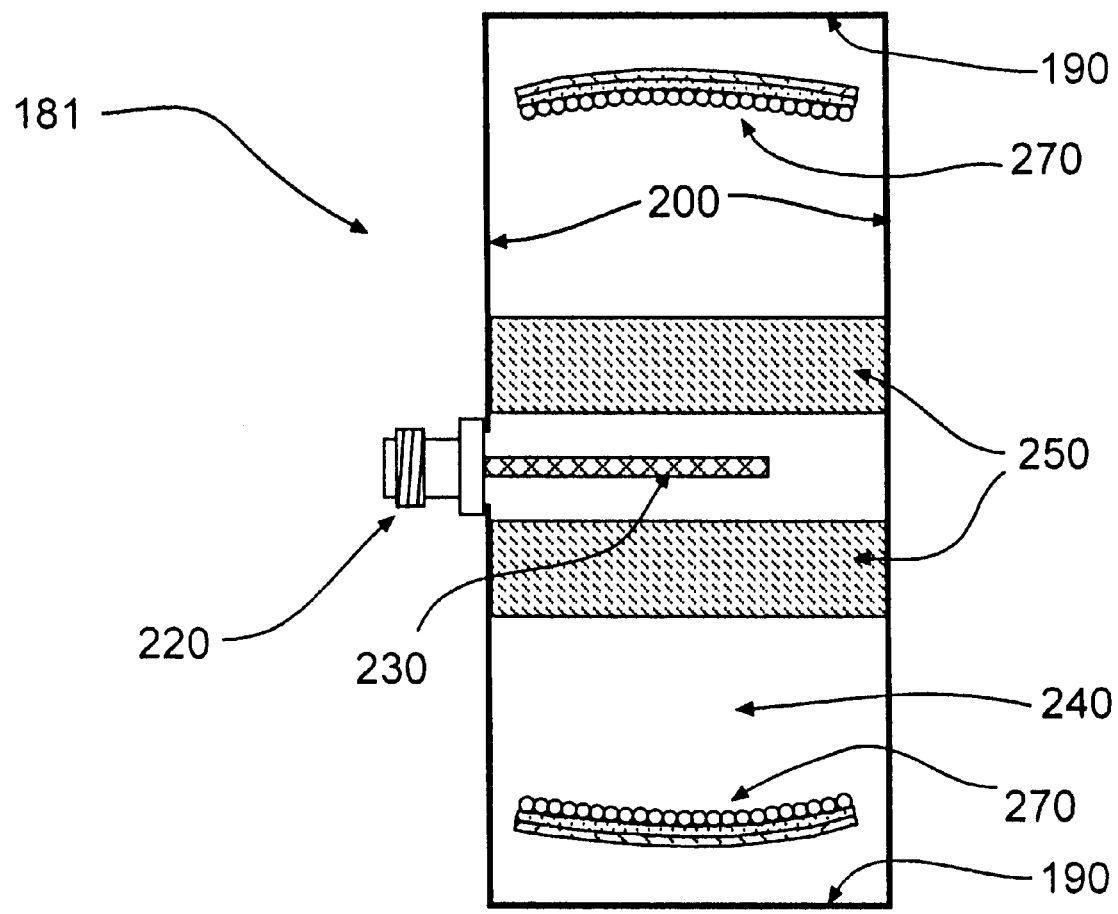
FIG. 15 is a cross-sectional view along the central axis of a chromatographic column microwave oven having a cylindrical resonant cavity in which the diameter of the column heating element varies axially.

Varying the diameter of the column heating element in a chromatographic column microwave oven alters its rate of microwave absorption along its length. FIG. 15 shows the cross section of a chromatographic column microwave oven 181 along its central axis having all of the same elements as the oven 180 shown in FIG. 11 except column heating element 270 replaces column heating element 130. The diameter of the column heating element 270 varies along its length (i.e., R(z) of the column heating element 270 varies while Ro(z) of the cavity wall 190 is constant and doesn't vary with z). R(z)/Ro(z) is smaller at the edges of the column heating element 270 than it is in the middle. Hence, it sees a higher field strength and absorbs more microwave power towards its ends than does the column heating element 130 in FIG. 11. This in turn changes the axial temperature profile of the column heating element 270 from that shown in FIG. 13. By varying the diameter of the column heating element 270 along its length, the temperature profile of the column in the column heating element 270 can be altered.

Figure 16:
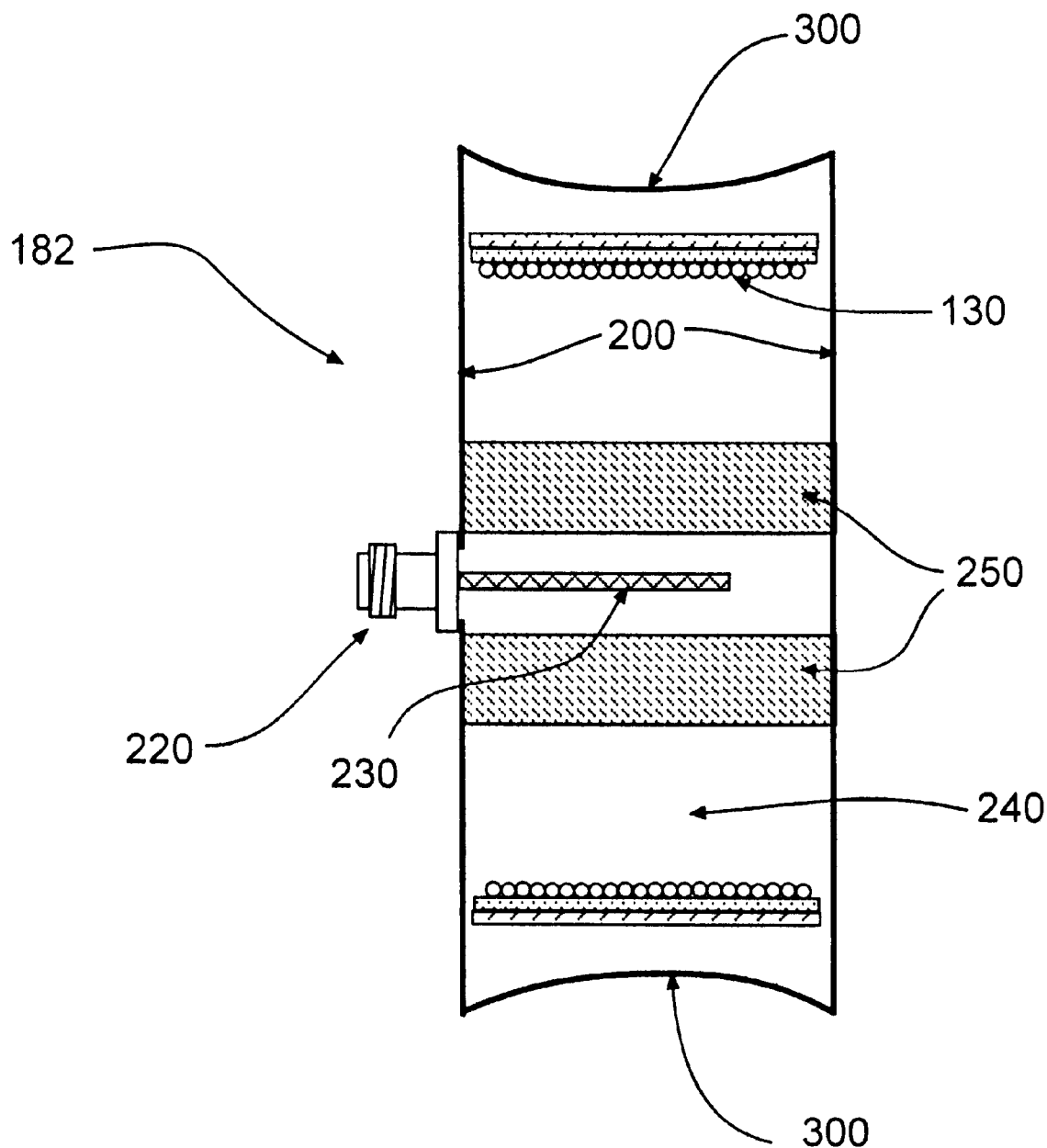
FIG. 16 is a cross-sectional view along the central axis of a chromatographic column microwave oven having a cylindrical resonant cavity in which the diameter of the cylindrical wall of the oven varies axially.

Varying the diameter of the cylindrical metal enclosure of a chromatographic column microwave oven along its length alters the rate of microwave absorption along the length of a column heating element in the oven. FIG. 16 shows the cross section of a chromatographic column microwave oven 182 along its central axis having all of the same elements as the oven 180 shown in FIG. 11 except the metal cylinder 190 is replaced with a metal enclosure 300 of circular cross section for which the diameter varies along its length. i.e. Ro(z) of the cavity wall 300 varies with z while R(z) of the column heating element 130 is a constant. Depending on the diameter of the enclosure 300 at its ends, the two end caps 200 may have different diameters. As with the oven 181, R(z)/Ro(z) is smaller at the edges of the column heating element 130 than it is in the middle. Hence, it sees a higher field strength and absorbs more microwave power towards its ends than does the column heating element 130 in FIG. 11. This in turn changes the axial temperature profile of the column heating element 130 from that shown in FIG. 13. By varying the diameter of the metal 'cylinder' 300 along its length, the temperature profile of the column in the column heating element 130 is also varied.

Figure 17:
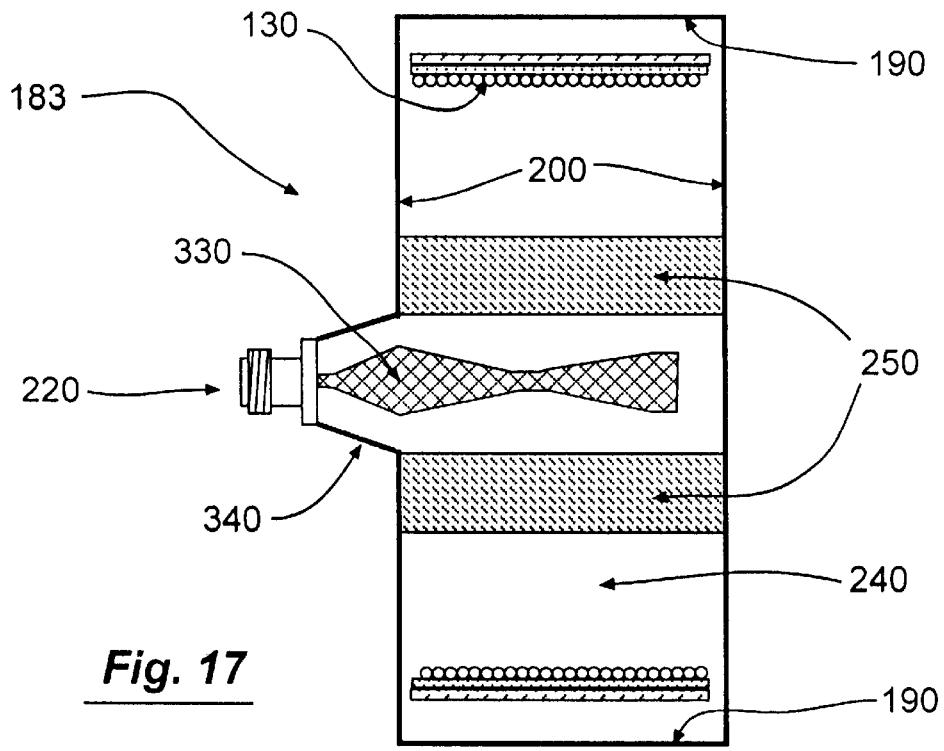
FIG. 17 is a cross-sectional view along the central axis of a chromatographic column microwave oven having a cylindrical resonant cavity in which the outer diameter of the antenna varies axially.

Varying the diameter of the antenna along its length in a chromatographic column microwave oven alters the rate of microwave absorption along the length of a column heating element in the oven. FIG. 17 shows the cross-section of a chromatographic column microwave oven 183 along its central axis having all of the same elements as the oven 180 shown in FIG. 11, except the antenna 190 is replaced with an antenna 330 having a diameter that varies along its length. R(z) of the column heating element 130 and Ro(z) of the cavity wall 190 are measured from the point of maximum electric field intensity in the cavity. The central antenna in a $TM_{010}$ resonant cavity is usually quite small in diameter as compared to the diameter of the cavity, so the point of maximum field intensity can be considered to be the central axis of the oven. However, the electric field intensity is actually highest at the surface of the antenna. In the oven 183, R(z) and Ro(z) are measured from the surface of the antenna 330 rather than from the central axis of the cavity at least at those axial points z where the antenna is present. As the diameter of the antenna 330 varies over its length, so too do R(z), Ro(z), and R(z)/Ro(z). R(z)/Ro(z) is smallest and microwave energy absorption highest in the column heating element 130 where the diameter of the antenna 330 is largest and vice-versa. By varying the diameter of the antenna 330 along its length, the temperature profile of the column in the column heating element 130 is also altered at least over the length of the antenna 330.

If the diameter of the antenna 330 is large with respect to the center conductor of the coaxial connector 220 where it passes through the end cap 200 and enters the resonant cavity, as shown in FIG. 17, then an impedance matching section 340 similar to the impedance matching sections 85 in FIG. 2 may be used to more gradually adjust the diameters of the inner and outer conductors before entering the cavity.

Figure 18:
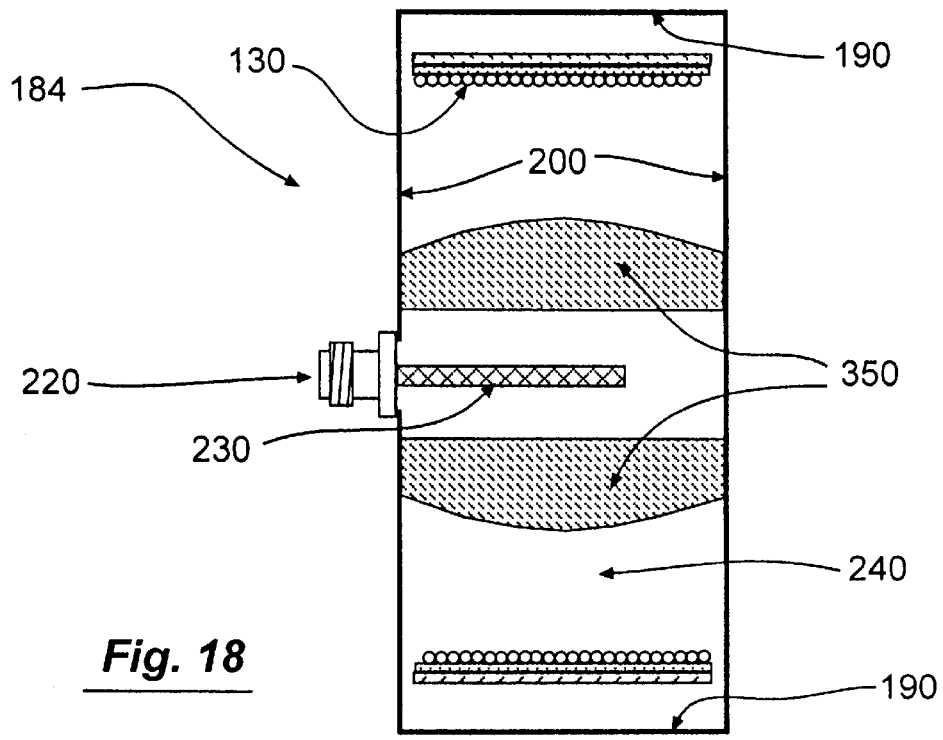
FIG. 18 is a cross-sectional view along the central axis of a chromatographic column microwave oven having a cylindrical resonant cavity in which the diameter of dielectric insert varies axially.

Varying the thickness of a cylindrical dielectric insert along its length in a chromatographic column microwave oven alters the rate of microwave absorption along the length of a column heating element in the oven. FIG. 18 shows the cross-sectional view of a chromatographic column microwave oven 184 along its central axis having all of the same elements as the oven 180 shown in FIG. 11, except the dielectric 250 is replaced with a dielectric 360 having a thickness that varies along its length.

The effective radii R(z) of a column heating element 130 and Ro(z) of a cavity wall 190 differ from the physical radii if the dielectric constant varies from the center of the cavity and out as it does when a dielectric insert is used. The electric field strength will decrease more through a given thickness of dielectric material in oven 184 than through an equivalent thickness of air or vacuum because its dielectric constant is higher. Thus, when a dielectric cylinder is used, Ro(z) and R(z) are greater than the physical lengths. If d(z) is the thickness of the dielectric 360 at a point z along its length, then the effective electrical radii of the column heating element 130 and the metal cylinder 190 depend on d(z) as well as z (i.e., R(z,d(z)) and Ro(z,d(z)) respectively). This effect was ignored when describing the oven embodiments 181, 182, and 183 because the thickness of dielectric 250 did not vary along its length. By varying the thickness of dielectric 360 along its length, the temperature profile of the column in column heating element 130 is similarly altered.

FIG. 15, 16, 17, and 18 show different oven embodiments in which the geometry of one of the elements is varied axially to adjust the axial distribution of microwave absorption in the respective column heating elements. The specific curvature shown for each varied element in these figures levels out the rate of electric field absorption in a column heating element as compared to that in the oven 180 shown in FIGS. 11 and 12, for which the temperature profile is as shown in FIG. 13. The curvature is reversed if the column heating element absorbs more energy from the magnetic field than from the electric field because the magnetic field strength in $TM_{010}$ resonators increases from a minimum at the center of the cavity to a maximum at the outer cylindrical boundary. This is the opposite of the electric field which decreases from a maximum at the center of the cavity to a minimum at the outer cylindrical boundary.

There is one other way to alter the rate of microwave energy absorption of the column heating element along its length. The rate of power absorption of a point in the column heating element is a function of the electromagnetic field strength and of the loss factor of the column heating element. The specific relationship is described by the following equation:

$$P_{av} = \omega \epsilon_0 \epsilon''_{eff} E_{rms}^2 + \omega \mu_0 \mu''_{eff} H_{rms}^2 \qquad (5)$$

where:

$\omega$ is the angular frequency of the electromagnetic radiation, $\epsilon_0$ is the permittivity of free space, $\epsilon''_{eff}$ is the dielectric loss factor, $E_{rms}$ is the rms electric field strength, $\mu_0$ is the permeability of free space, $\mu_{eff}$ is the magnetic loss factor, and $H_{rms}$ is the rms magnetic field strength.

By varying the dielectric or magnetic loss factor of a column heating element along the its length such that one has $\epsilon''_{eff}(z)$ or $\mu''_{eff}(z)$, the axial power absorption and the resulting temperature profile of the column in the column heating element are similarly altered.

It may not be practical to achieve perfect isothermal conditions along the length of a chromatographic column assembly in a microwave oven owing to the interaction of the microwave absorbing material and the electromagnetic field. However, temperature variations can certainly be minimized such that conditions substantially equivalent to isothermal conditions are achieved.

The usage of thermally conductive material within the column heating element can help redistribute thermal energy if there are variations in temperature within the column heating element. Thus, thermally conductive material can be used to augment and improve the effectiveness of the various methods described herein for controlling the rate of microwave energy absorption throughout a column heating element. Thermally conductive material used in a column heating elements in chromatographic column microwave oven must not be electrically conductive or it will disrupt the proper operation of the oven.

Figure 19:
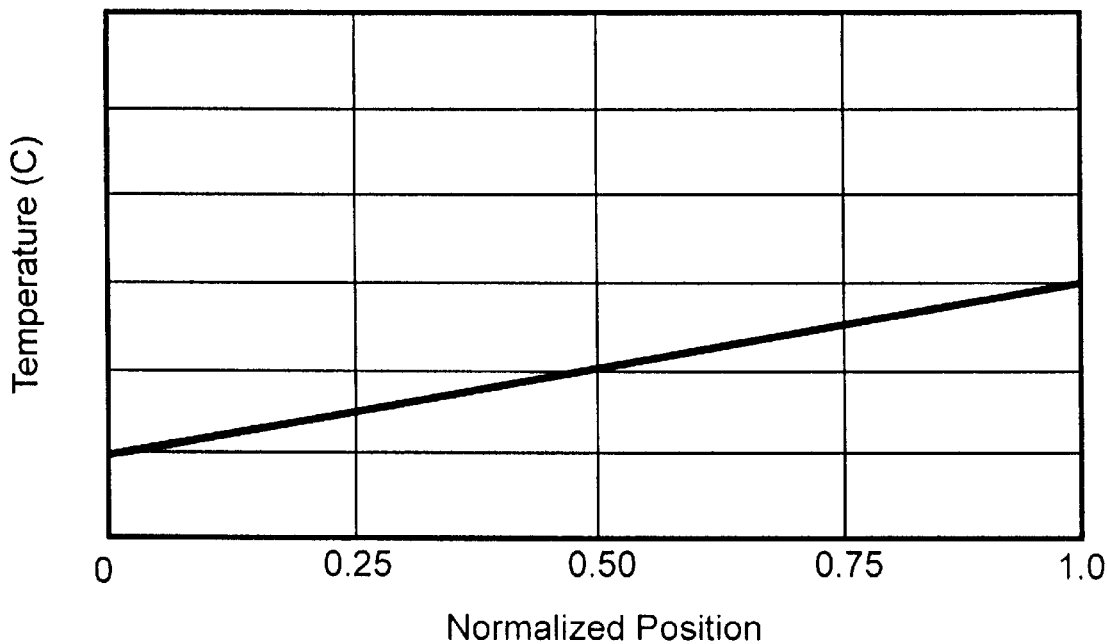
FIG. 19 is a graph showing a linearly increasing column temperature profile.
Figure 20:
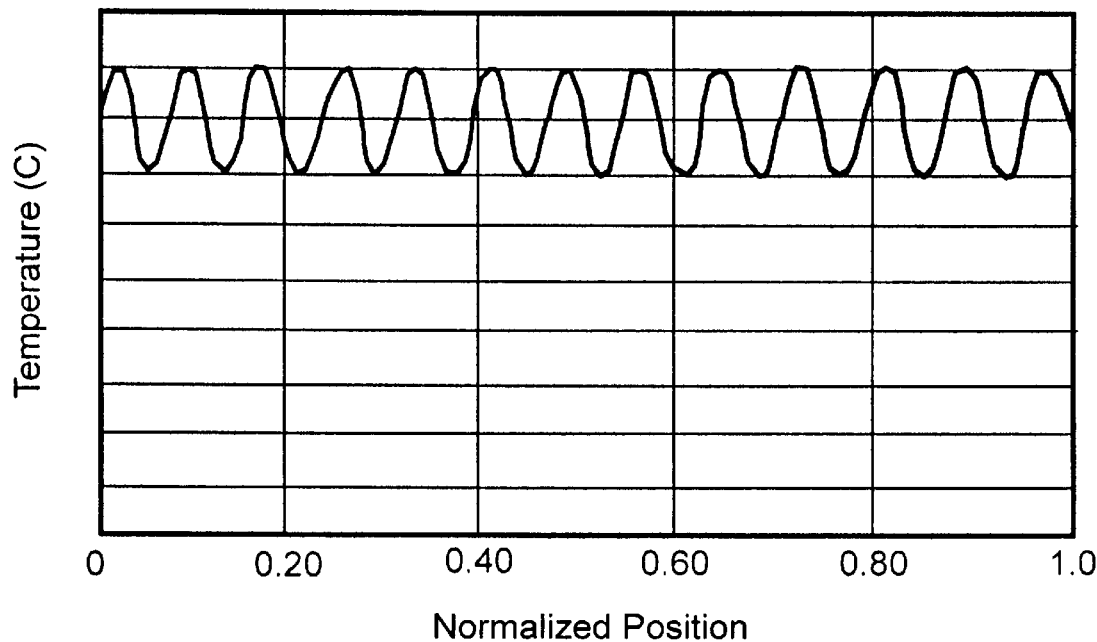
FIG. 20 is a graph showing a periodic column temperature profile.

Isothermal temperature profiles are usually used in chromatographic analyses. In fact, no other profile is used within the large resistively heated ovens used in most gas chromatographs. However, other temperature profiles can be achieved within the chromatographic column microwave ovens taught herein. For example, a microwave oven could be designed utilizing the methods and apparatus taught herein to achieve a linear temperature profile in a chromatographic column as illustrated in FIG. 19. Another useful temperature column profile that can be readily obtained with the microwave ovens described herein but which cannot be achieved in existing chromatographic column ovens is a periodically varying profile such as that shown in FIG. 20.

A periodically varying column temperature profile can improve the separation of components having small retention time differences because these components can pass many times through a temperature zone critical to separation during a single analysis. In a standard chromatographic oven using conventional temperature ramping programs, the critical temperature zone can only be passed through one time. Consider two compounds for which R1 represents the retention time of a first compound in a given chromatographic column and R2 represents the retention time of a second compound. Assume, that the boiling point of the first compound is higher than that of the second compound. The ratio of retention times of the two compounds R1/R2 forms the basis for their separation. At temperatures well above and well below the boiling points for the two compounds, the ratio R1/R2 is essentially one, so that no separation occurs. As the temperature of the column is increased from a cold point, the value of R1/R2 will increase until reaching a maximum at the temperature at which the compounds can most readily be separated and resolved. When a column has a periodic temperature profile, the compounds pass through the temperature corresponding to the maximum value of R1/R2 many times during a single analysis instead of just once, thereby improving separation and resolution.

All of the methods described herein to alter the axial microwave absorption distribution of a column heating element can be used to engineer a specific temperature profile along a chromatographic column including essentially isothermal, linear, or periodic profiles.

Figure 21:
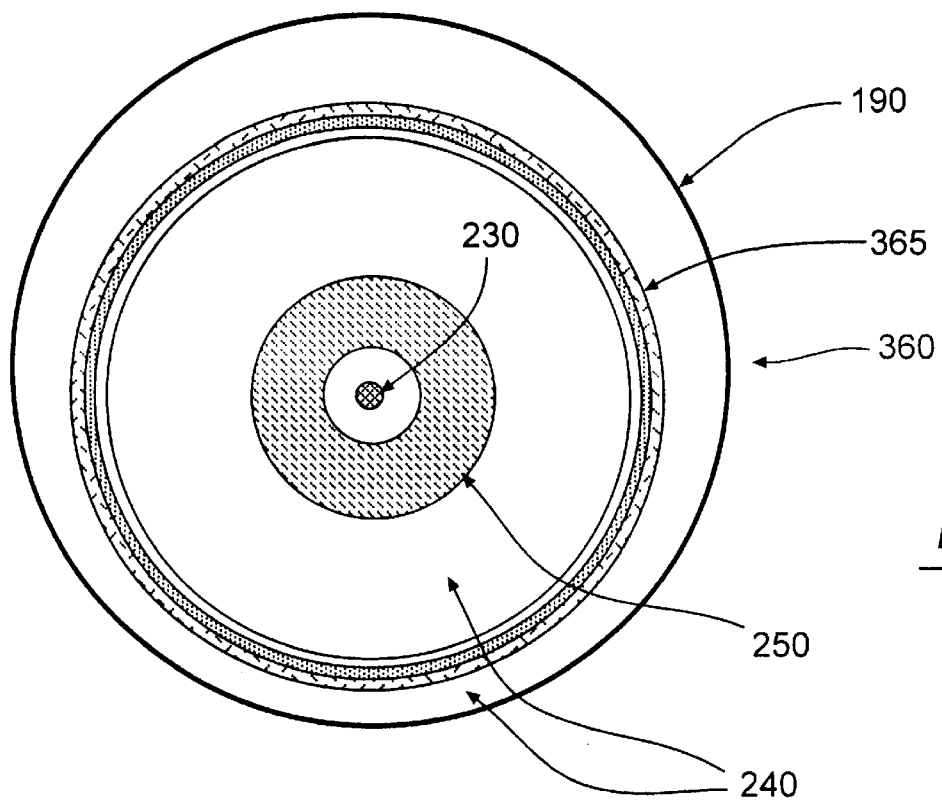
FIG. 21 is a radial cross-sectional view of a chromatographic column microwave oven wherein the column heating element is positioned off center within the oven in order to establish a periodic column temperature profile.

There are several other simple methods with which a periodic column temperature profile can be achieved in a microwave oven as taught herein. One method is to physically offset an element of the chromatographic column microwave oven from the center of the oven in order to displace the central axis of the column heating element from the central axis of the electromagnetic field. FIG. 21 shows the radial cross section of an embodiment of a chromatographic column microwave oven 360 in which the column heating element 365 has been offset from the geometric center of the oven. Such an offset will result in a temperature profile along each column coil in the heating element 360. This temperature profile will be repeated in each subsequent coil resulting in an overall periodic column temperature profile. A similar effect would be achieved if the column heating element is positioned symmetrically about the geometric center of the oven but the antenna 230 is moved off center, or the dielectric insert 250 is moved off center, or if some other object is placed off center within the oven so as to disturb the symmetry of the oven and thereby displace the center of the electromagnetic field from the central axis of the column heating element.

Figure 22:
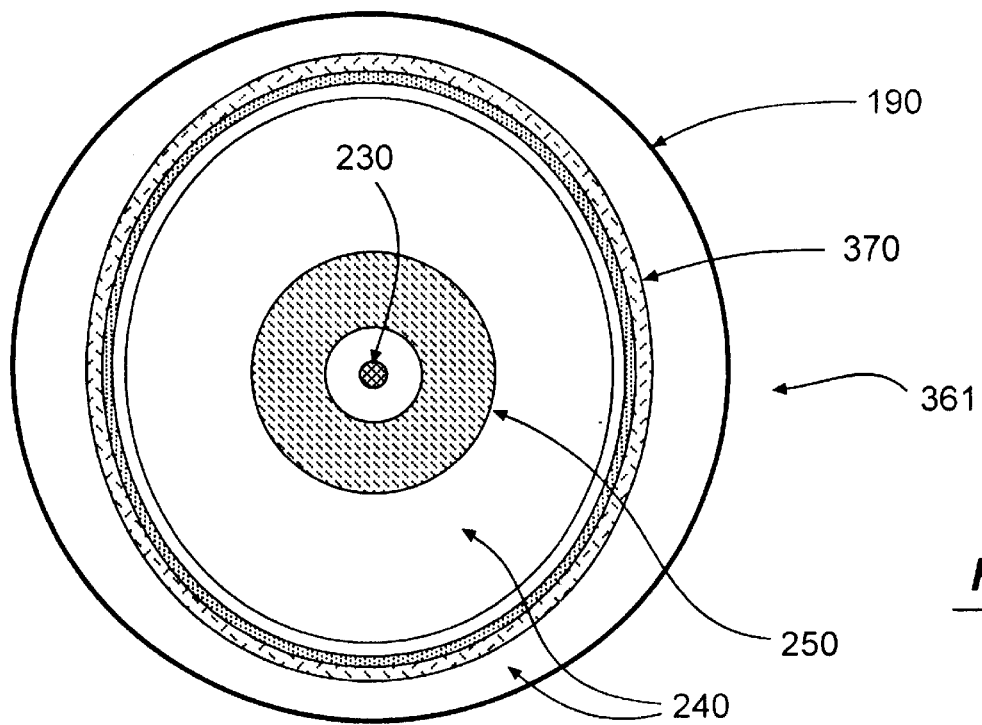
FIG. 22 is a radial cross-sectional view of a chromatographic column microwave oven wherein the column heating element has a different shape than does the oven in order to establish a periodic column temperature profile.

A second method for establishing a periodic column temperature profile is to alter the cross-sectional shape of the column heating element with respect to that of the oven so that individual coils do not trace isofield lines within the oven but rather oscillate about such lines resulting in a periodic column temperature profile. FIG. 22 shows the radial cross section of an embodiment of such a chromatographic column microwave oven 361 in which the column heating element 370 has an oval cross section while the oven walls 190 have a circular cross section. The same effect is achieved if the heating element 370 has a circular cross-section while the oven wall 190 or the dielectric insert 250 has a non-circular cross-section.

A last method for generating a periodic column temperature profile in a column heating element is to radially vary the electrical or thermal properties of the heating element so as to radially vary the heating rate that occurs in the heating element and thereby induce a periodically varying column temperature profile.

Using the chromatographic column microwave ovens taught herein, the column temperature profile can be engineered to optimize the quality of the chromatographic analyses. It should be clear that the column temperature profiles that can be established are not limited to those specifically described. Many other profiles can be created using the present invention.

Common Elements of the Chromatographic Column Microwave Oven Embodiments

A number of chromatographic column microwave oven embodiments have been described heretofore in this invention including coaxial microwave ovens and circular cylindrical resonant cavity ovens. Each of these oven embodiments may require implementation of at least one of the techniques taught for modifying the axial electromagnetic field gradient to make it a practical and useable chromatographic column microwave oven. There are certain common characteristics of useful chromatographic column microwave ovens as taught in this invention with which controlled column temperature profiles can be achieved:

(1) Each oven is a single mode structure. Multiple modes and the uncertain electromagnetic field distribution that result therefrom are avoided.

(2) The cross sectional geometry of each oven about its central axis results in an electromagnetic field distribution characterized by smoothly varying, continuous isofield lines oriented about an axis which is typically collinear with the geometric central axis of the oven. A chromatographic column coiled in a column heating element which traces these isofield lines is thus exposed to an electromagnetic field strength that is constant over the length of each individual column coil. Consequently, each such coil absorbs microwave energy at substantially the same rate at all points along its length. Each single chromatographic column coil is thus an isotherm or very nearly so given the small change in axial position between adjacent coils. Similarly, a column heating element that is placed in the oven in such a way that each coil of column traces a line which oscillates about the isofield lines is exposed to a periodically varying electromagnetic field strength that results in an oscillatory column temperature profile.

Figure 23:
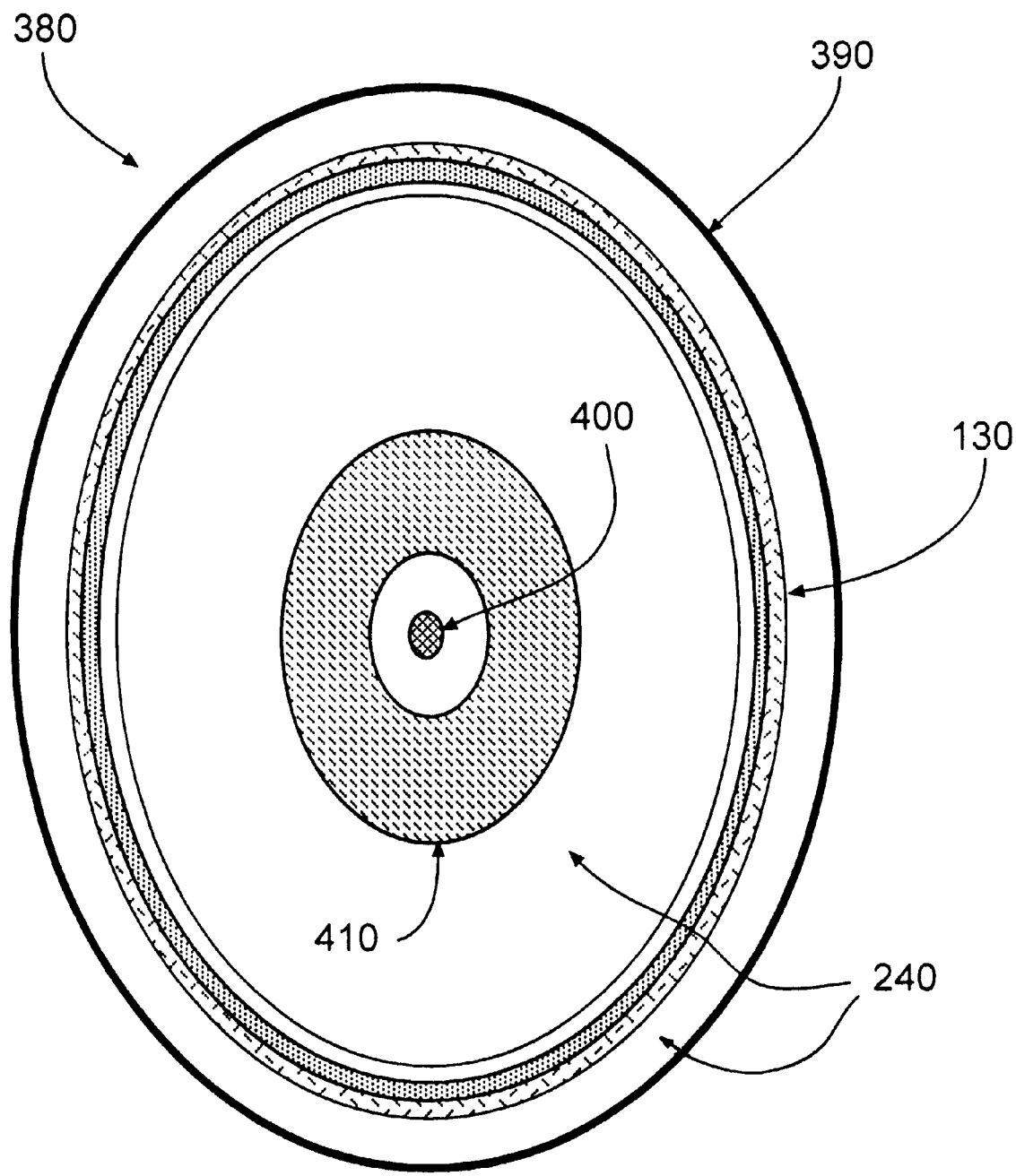
FIG. 23 is a cross-sectional view along the central axis of a chromatographic column microwave oven having an elliptical shape rather than a cylindrical shape.

All of the chromatographic column ovens described heretofore have circular cross sections perpendicular to the central axis as have the associated column heating elements. It is certainly possible to deviate from a circular structure and still have each column coil be an isotherm. A column coil will be an isotherm if it follows an isofield line in the oven. FIG. 23 shows the cross section of an elliptical chromatographic column oven 380 perpendicular to its central axis wherein the outer metal enclosure 390, the optional dielectric 410, and the antenna 400 are all elliptical. The electromagnetic field lines within the oven 380 will tend to follow the elliptical shape of the metal enclosure 390. As the column heating element 130 is elliptical, each column coil within the heating element 130 will still be an isotherm It should be understood that the present invention incorporates all chromatographic column microwave oven structures within which individual column coils either: (a) closely follow isofield lines within the oven such that the temperature varies little along the length of each column coil; or (b) oscillate about such isofield lines within the oven such that the temperature varies periodically along the length of the column coils.

(3) To achieve the desired chromatographic column temperature profile in a microwave oven, the electromagnetic field gradient from one coil of the column in the column heating element to the next must be sufficient to achieve the desired temperature difference from one coil to the next. If conditions approaching isothermal conditions are desired in the column, then the rate of microwave absorption must be substantially equal over the whole length of the column. To achieve this, the oven must be constructed using the techniques taught in this patent to expose the column heating element to the appropriate electromagnetic field strength along its length.

Compact Chromatographic Column Microwave Oven

As noted previously, chromatographic columns are very small—having diameters as little as 0.1 mm. All chromatographic column microwave oven embodiments described heretofore heat thin, cylindrical column heating elements which can be treated as two dimensional surfaces over which desired temperature conditions are established. These heating elements are thin because the column itself has a small diameter and because the column coil is only one or at most a few column layers in thickness. Problems associated with slow thermal conductivity in insulating materials are minimized with such column heating elements. However, even smaller microwave ovens can be constructed if the chromatographic column is bundled more tightly together or etched into a rigid substrate such as silicon.

Radiative heat loss from the chromatographic column during the heating cycle can be greatly reduced by providing the oven cavity with an infrared-reflective interior surface. For example, the interior surface of the cavity can be made of polished aluminum or steel.

Figure 24:
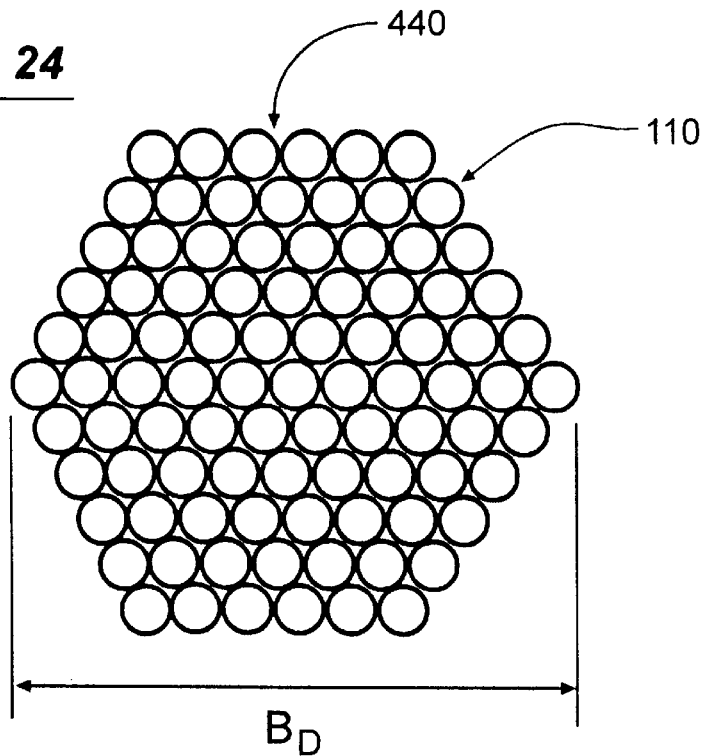
FIG. 24 is the cross-sectional view of a tightly bundled coil of chromatographic column.
Figure 25:
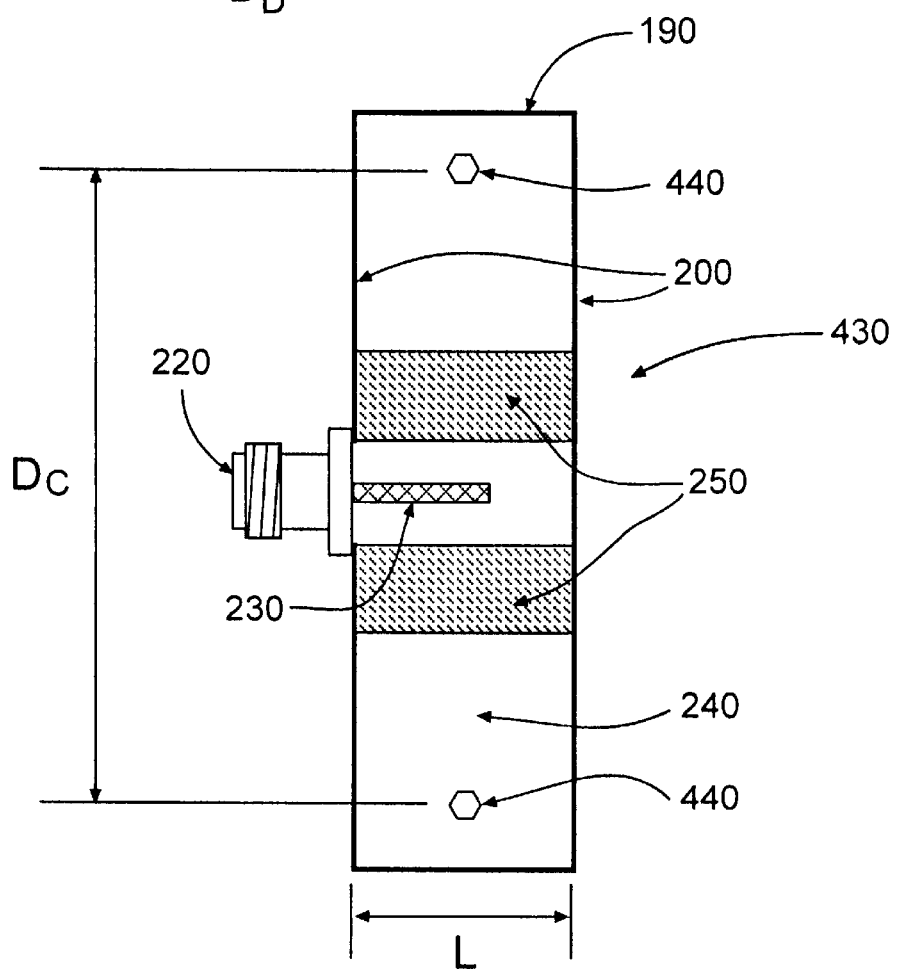
FIG. 25 is a cross-sectional view along the central axis of a compact chromatographic column microwave oven.

FIG. 24 shows the cross section of a chromatographic column 110 tightly packed into a coiled chromatographic column bundle 440 where the diameter of the filament bundle is denoted $B_D$. When packed in this manner, a 50 m long 0.32 mm diameter column coiled into loops 12.5 cm in diameter can be packed into a bundle for which $B_D$ is approximately 4.1 mm. FIG. 25 shows the cross section of a chromatographic column microwave oven 430 along its central axis in which a column bundle 440 having a major diameter $D_C$ is heated. The oven 430 has the same components as does the oven 180 shown in FIG. 11 and 12 except for the substitution of column bundle 440 for column heating element 130. Column bundle 440 must contain microwave absorbing material if it is to absorb microwave energy and be heated in the oven 430. This microwave absorbing material can be incorporated into the column 110 itself, as disclosed in the Applicant's co-pending U.S. patent application Ser. No. 09/108,297, or dispersed within the column bundle 440 adjacent to the column 110.

Because $B_D$ is so small, the length L of oven 430 can be smaller than is possible with the other oven embodiments described in this invention. The axial length of the heating section could be as small as 5 to 10 mm though the diameter would still be at least several centimeters.

Though $B_D$ of a column bundle 440 is very small, the electromagnetic field strength to which it is exposed in the oven 430 will still vary over its cross section unless its loss factor is so small as to make it impractical for microwave heating purposes. Consequently, there will be variation in the rate at which microwave energy is absorbed in a column bundle 440 and the temperature will vary along the length of column 110. This variation cannot be corrected by changing the geometry of the oven 430.

Because the filament 440 is as small as it is, thermal energy redistributes itself relatively quickly to establish a thermal equilibrium approaching isothermal conditions. Carrier gas flowing within the column 110 further helps to redistribute heat within the bundle 440. Adding thermally conductive material to the column bundle 440 will accelerate the rate at which thermal equilibrium is reached and ensure that the equilibrium approaches isothermal conditions as closely as possible.

While it may not be possible to achieve true isothermal conditions in the chromatographic column microwave oven 430, it is physically the most compact oven embodiment using commercially available capillary columns taught in this invention.

Connecting the Column Ends to the Injector and Detector

To incorporate the chromatographic column microwave oven embodiments taught herein into the rest of a gas chromatograph, the ends of the column must be connected to the injector and detector assemblies respectively, neither of which is conveniently placed in the microwave oven. These column ends must be kept at a temperature at least as high as the bulk of the column being heated in the microwave oven to prevent cold spots which, if present, severely degrade the performance of the GC. The injector and detectors themselves are maintained at temperatures above that of most of the column.

Figure 26:
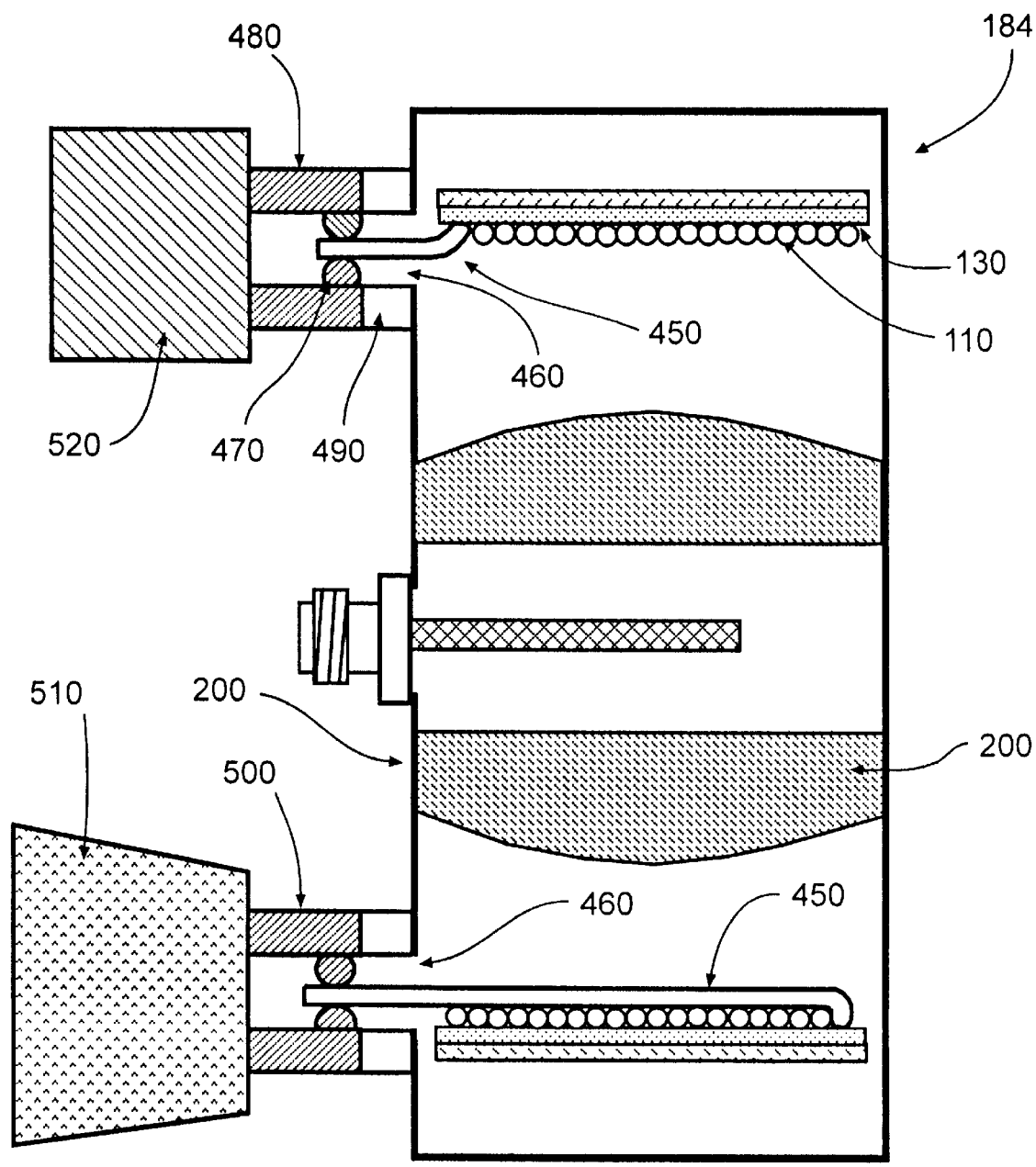
FIG. 26 is a cross-sectional view along the central axis of a chromatographic column microwave oven illustrating how the ends of the chromatographic column are connected into the injector and detector assemblies.

FIG. 26 shows how the chromatographic column microwave oven 184 can be incorporated into a chromatograph without inducing cold spots. The column ends 450 of the column 110 leave the microwave oven 184 through the holes 460 in the metal end cap 200 and enter the adapters 500. The adapters 500 provide mechanical connections between the chromatographic column microwave oven 184 and the injector 510 and the detector 520 respectively Each adapter 500 consists of: (1) a metal fitting 480 which is kept in intimate thermal contact with the injector 510 or the detector 520 housings; (2) a chromatographic column ferrule seal 470 which fits tightly within the metal fitting 480 and through which the column end 450 protrude; and (3) a thermal insulator fitting 490 which fits tightly between the metal fitting 480 and the end cap 200. The ferrule seal 470 is kept in thermal contact with the metal housing 480 so that it is essentially the same temperature as the injector 510 or the detector 520 respectively. The column ends 450 should not come into physical contact with any parts between the ferrule seal 470 and the column heating element 130 as any such parts are likely to be colder than the column ends 450 and therefore will conduct heat away from the column ends 450 creating cold spots in the column. The insulator fitting 490 slows the flow of heat from the metal fitting 480 to the end cap 200. Excess heat in the end cap 200 can slow the cooling rate of the oven 184 after the heating cycle is completed.

The interior of the oven 184 should be vacuum tight. The ferrule seal 470 is used as a vacuum seal on the exterior of both the column ends 450. Thus, the interior of the column 110 is not depressurized and the carrier gas and sample to be analyzed can pass freely through the column 110 from the injector 510 to the detector 520. The ferrule seal 470 is vacuum sealed to the metal fitting 480 which in turn is vacuum sealed to the insulator fitting 490. Finally, the insulator fitting 490 is vacuum sealed with the end cap 200. These different seals isolate the interior of the oven 184 from the injector 510 and the detector 520 and make it possible to operate the oven 184 in vacuum.

Figure 27:
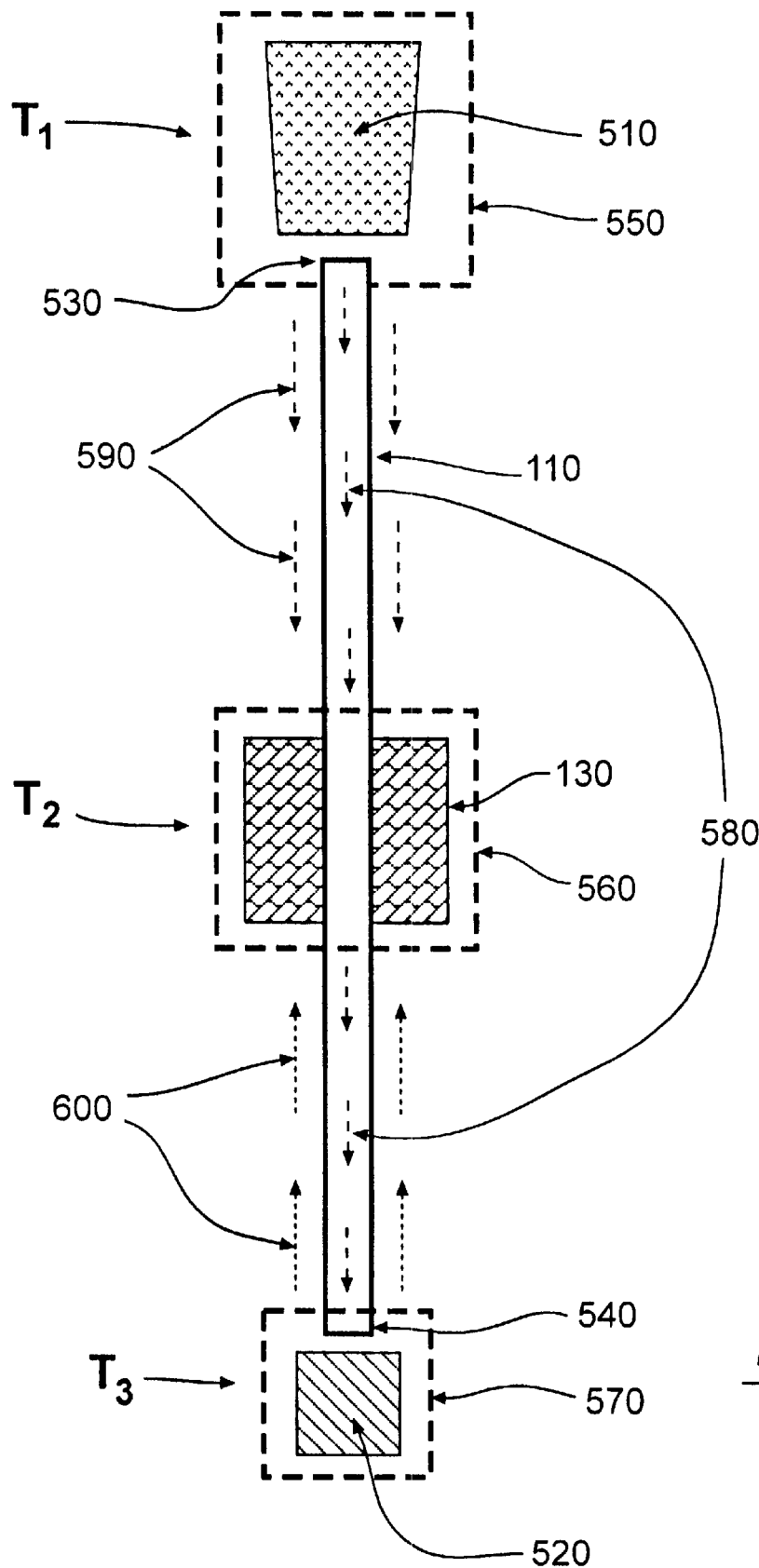
FIG. 27 is a diagram illustrating how the heat flows in the column within a microwave oven.

Several thermal processes occur within the structure illustrated in FIG. 26 that heat the column ends 450 while operating the chromatographic column microwave oven 184 even though the column ends 450 may not be heated directly by the column heating element 130. These processes are illustrated in FIG. 27.

Block 550 designates one isothermal region maintained at temperature T1. Block 550 includes the injector 510 and the proximal column end 530 of chromatographic column 110. Block 560 designates a second isothermal region (assuming an isothermal temperature profile for this description) having a temperature T2. Block 560 includes the column heating element 130. Block 570 designates a third isothermal region maintained at temperature T3. Block 570 includes the detector 520 and the distal column end 540 of chromatographic column 110. In a typical chromatography application, the detector 520 is kept hotter than the injector 510 which in turn is kept hotter than most of the chromatographic column 110, giving T3>T1>T2.

Thermal conduction and convection processes transfer thermal energy to those lengths of column 110 not heated directly in the blocks 550, 560, or 570. These processes are significantly more efficient if the chromatographic column microwave oven is operated in vacuum conditions.

Conduction. The thermal energy 590 is conducted along the walls of the column 110 from the block 550 to the block 560 because T1 is greater than T2. A similar flow of thermal energy 600 is conducted from the block 570 to the block 560 in the walls of the column 110. The thermal conduction processes 590 and 600 are very slow unless the column 110 includes a thermally conductive material to improve the thermal transfer rate.

Convection. A significantly faster heating mechanism for the column ends than direct conduction is convection from the carrier gas 580 flowing in the column 110. The carrier gas 580 flowing into the column 110 from the injector 510 will be the same temperature as the injector—T1. The flowing carrier gas stream 580 rapidly heats the length of column 110 lying between the isothermal blocks 550 and 560. Once the carrier gas stream 580 reaches the isothermal block 560, it rapidly comes to an equilibrium temperature of T2. The carrier gas stream 580 flowing from the block 560 rapidly heats the length of column 110 lying between the isothermal blocks 560 and 570.

If the lengths of the column 110 between the isothermal blocks 550 and 560 and between the blocks 560 and 570 respectively are surrounded by relatively cool air, most of the thermal energy in the column will be lost to the air and the column ends will not be heated significantly by the described conduction and convection processes. This is yet another reason for operating the chromatographic column microwave ovens taught herein in vacuum conditions.

Figure 28:
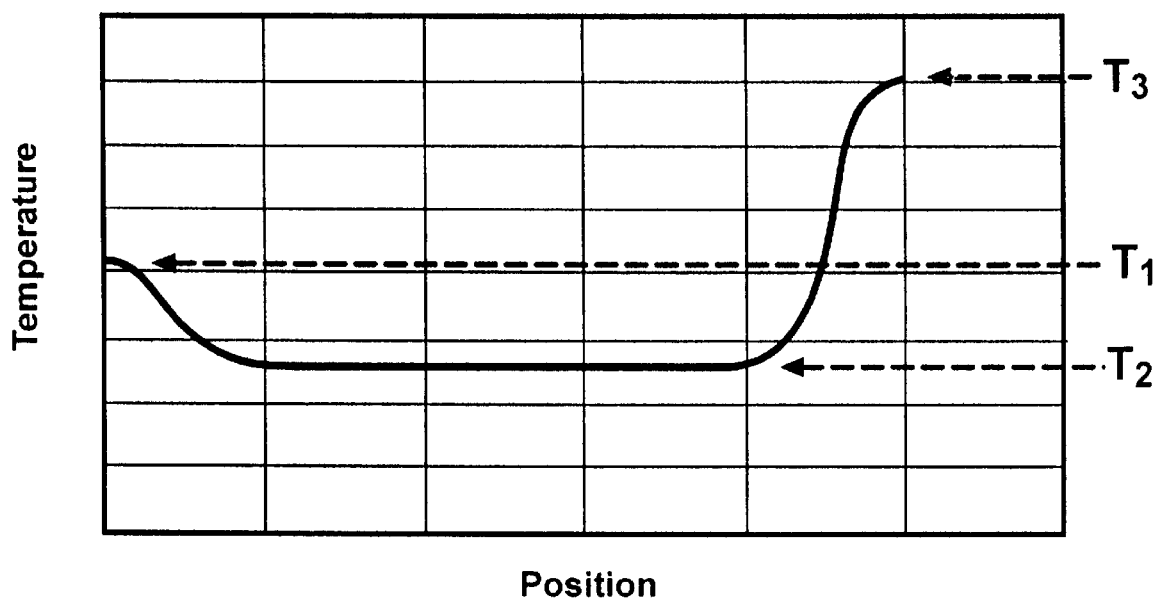
FIG. 28 is a graph illustrating the end-to-end temperature profile along a column heated within a microwave oven.

At thermal equilibrium, the temperature profile established along the entire length of the column 110 in a chromatographic column microwave oven as taught herein is similar to that established along a column in a conventional chromatographic oven. The profile is illustrated in the graph shown in FIG. 28 in which the x-axis represents the position along the length of the column 110 and the y-axis represents the column temperature. The x-axis is not to scale as the relative length of the column maintained at T2 would typically be much longer than the rest of the column. Starting from the left side of the graph, the temperature of the proximal end of the column 110 is equal to T1 which is the temperature of the injector 510. Moving to the right, the temperature of the column 110 drops to a temperature of T2 which is the temperature of the column heating element 130. The temperature of the column 110 is equal to T2 through the whole of the column heating element 130. After the column heating element 130, the temperature of the column 110 increases to a temperature at its distal end of T3 which is the temperature of the detector 520. Along the whole length of the column 110, there are no cold spots at which the temperature drops below T2.

Maximizing Thermal Efficiency in the Oven

The total amount of thermal energy that a chromatographic column oven needs to supply to a column heating element to attain a desired temperature is described by the following equation:

$$P_{TOT} = \Sigma M_i C_{pi} \Delta T/t + P_{CONV} + P_{COND} + P_{RAD} \quad (6)$$

where $P_{TOT}$ is the total thermal power input of the oven, $M_i$ is the mass of each part 'i' in the oven that is to be heated, $C_{pi}$ is the specific heat of each part 'i', $\Delta T/t$ is the target rate of temperature increase per unit time, $P_{CONV}$ is the heat transferred from the heated parts of the oven to other parts and to the environment by convection processes.

$P_{COND}$ is the heat transferred from the heated parts of the oven to other parts and to the environment by direct thermal conduction mechanisms.

$P_{RAD}$ is the heat transferred from the heated parts of the oven to other parts and to the environment by radiative processes.

As is clear from Eq. (6), the energy requirements of a chromatographic column oven can be minimized by: (1) minimizing the mass of the material that is heated so as to minimize the energy required to increase its temperature and (2) minimizing the thermal energy losses from the heated portions of the oven. Direct microwave heating of an appropriately designed column heating element makes it possible to reduce the mass of the material to be heated to little more than that of a standard chromatographic column. Thus, a chromatographic column microwave oven can minimize the amount of power needed to heat up a column. To achieve maximum efficiency, thermal losses from the column heating element must also be minimized.

As described previously, thermal losses via convection are best minimized by removing most of the air from the interior of the chromatographic column microwave oven. Even a modest vacuum of 75 Torr will reduce convection losses by 90%.

Thermal conduction losses from the heated portion of the column heating element to the walls of the oven are easily reduced by properly designing the mechanical support assembly which holds the column heating element within the oven. The mechanical support should be constructed from materials which can withstand exposure to high temperature, have low thermal conductivity, do not absorb microwave energy appreciably, and which will not disturb the electromagnetic field distribution within the microwave oven. Appropriate materials include many ceramics such as aluminum oxide and high temperature plastics such a polyimide. In addition, the cross sectional area of the mechanical supports which physically connect the heated portion of the column heating element to the oven walls should be reduced as much as is practical to minimize the flow path through which thermal energy can conduct to the oven walls.

When thermal loss via convection and conduction have been reduced as described, radiative losses from the column heating element represent the most significant source of thermal loss from the column. Radiative losses from the column heating element are directly proportional to the surface area of the heating element and the emissivity of the material on the surface of the heating element. The surface area of the heating element is most easily reduced by wrapping the chromatographic column into a bundle as illustrated in FIG. 24 and utilized in oven 430 as shown in FIG. 25. Reducing the emissivity of the heating element is not very practical, however.

Emissivity is a unitless coefficient having a value between 0 and 1. It represents how much a given material radiates at a given temperature as compared to a perfect black body source which has an emissivity value of 1. Electrically non-conducting materials such as plastic and ceramic typically have emissivity values of 0.9 or greater. As these materials are the most suitable for usage in a column heating element in chromatographic column microwave oven, it is not practical to significantly reduce direct radiative losses of a column heating element by using materials with low emissivity values. However, radiative losses can be reduced indirectly.

Most radiation emitted from a hot column heating element will strike the interior surface of the metal walls of the microwave oven. Most metals have emissivity values less than 0.2 and so are poor emitters of thermally induced radiation. But they are good reflectors of this same radiation because the reflection coefficient for different materials is related to (1−emissivity). Consequently, most of the thermal energy radiated by a column heating element which strikes the metal walls of the oven is not absorbed by the walls but is reflected back into the oven. Thus, if the emissivity of the interior surface of the microwave oven walls is minimized, then the radiative loss from the column heating element will similarly be minimized because most of the energy radiated by the heating element will be internally reflected in the oven until it strikes a surface with a high emissivity value where it will be absorbed. Most thermal radiation emitted by the column heating element will find its way back to the column heating element. The bath of thermal radiation with the oven also helps heat the column ends.

The emissivity of the interior walls of the oven can be minimized by: (1) using a material with a low emissivity value such as aluminum, gold, copper or silver; and (2) by polishing the walls to reduce surface roughness. A well polished gold surface has an emissivity value of less than 0.02. The entire wall need not be made of a precious metal such as gold to achieve the desired effect. A thickness on only a few micrometers is sufficient.

When all of the measures are taken to reduce thermal losses, a high efficiency chromatographic column microwave oven is achieved. Less than 100 W of microwave power are required to maintain the temperature of a typical 60 m chromatographic column at 350° C. as compared to more than 1500 W with a typical resistively heated chromatographic oven. With so little energy to be dissipated, the walls of the oven do not get very warm even when uninsulated. This is a significant advantage as compared to other column heating methods.

Controlling the Microwave Source used to Drive the Oven

Figure 29:
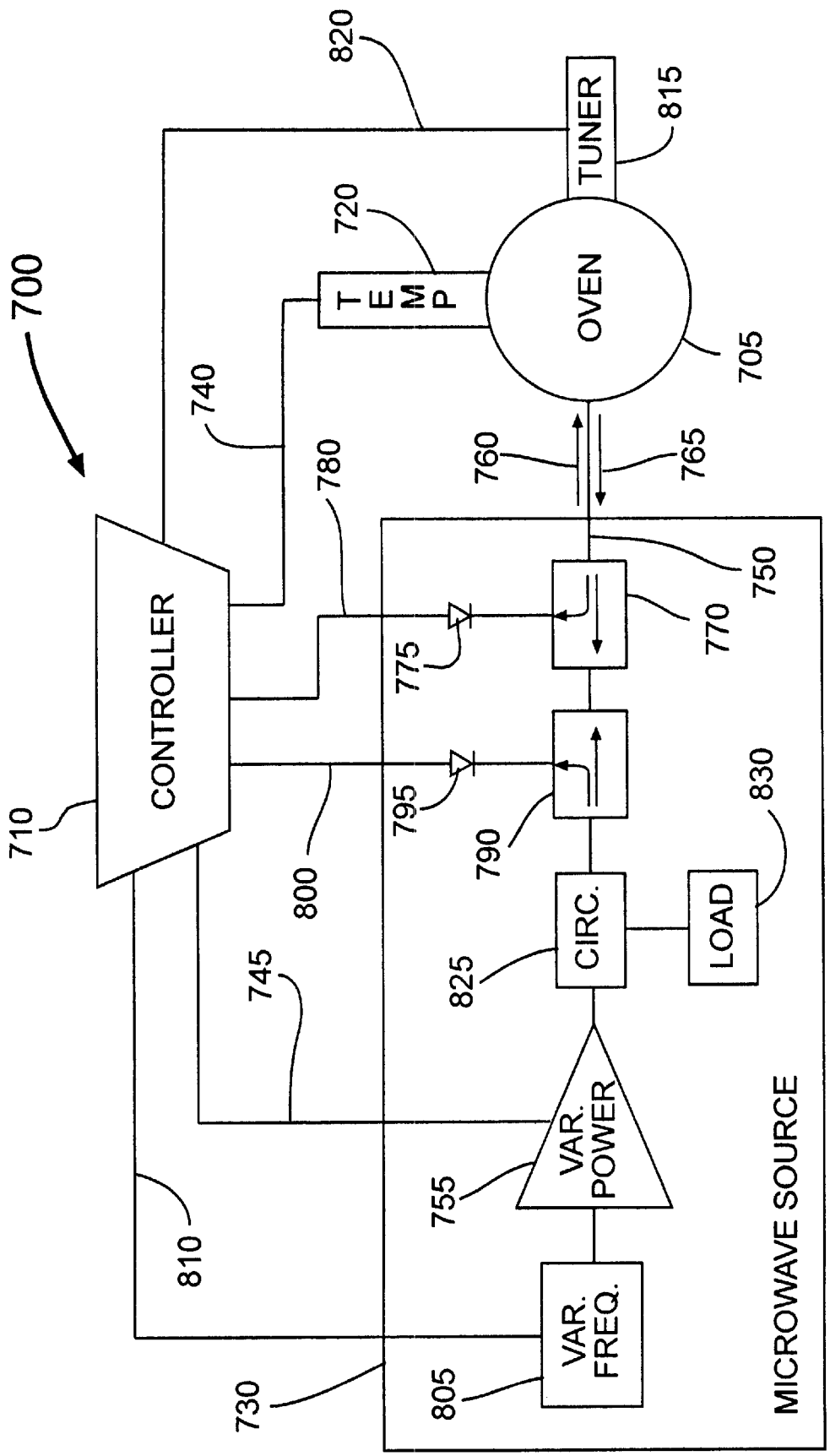
FIG. 29 shows an system which can control the temperature of a column in a chromatographic column microwave oven and which can control the efficiency of the microwave power source.

A chromatograph which includes a chromatographic column microwave oven must continuously control the temperature of the column heating element in the oven in order to generate useful temperature ramps. Continuous oven temperature control is achieved via control of the microwave source used to generate the microwave signal that is transmitted into the oven. FIG. 29 shows a system 700 capable of: (1) controlling how much microwave power is transmitted to a chromatographic column microwave oven; and (2) controlling the power efficiency of the microwave source. The main components of system 700 are a microwave oven 705, a controller 710, a temperature sensor 720, and a microwave source 730. The oven 705 is any microwave oven used to heat a chromatographic column. The controller 710 is understood to be any electronic system or computer capable of receiving input signals and generating output signals in response to the inputs in accordance with preprogrammed instructions. The temperature sensor 720 is any temperature measurement apparatus with which the temperature of the chromatographic column within oven 700 can be determined. The microwave source 730 is any microwave signal generator capable of producing enough microwave power to heat a chromatographic column in oven 705. For the purposes of this description, the microwave source 730 includes all components used to generate, amplify, attenuate, modulate, monitor, or otherwise alter the microwave signal transmitted to the oven 705.

The controller 710 is connected to the temperature sensor 720 by a signal line 740. The controller 710 is connected to the microwave source 730 by a signal line 745. The microwave source 730 generates and transmits a microwave power signal 760 to the oven 705 via a transmission line 750. The temperature sensor 720 measures the temperature within the oven 705 and transmits a corresponding signal to the controller 710 via signal line 740. If the temperature is too low, the controller 710 increases the microwave power signal 760 being transmitted to the oven 705 by adjusting a variable power element 755 within the microwave source 730 via control line 745. Similarly, if the temperature is too high, the microwave power signal 760 is correspondingly reduced. The variable power element 755 is any component by which the output power of the microwave source 730 can be adjusted, including but not limited to variable gain amplifiers, variable attenuators, and circuits which essentially turn the microwave power on and off such that the total microwave output power is modulated by controlling the duty cycle. Together, the controller 710, temperature sensor 720, and variable power element 755 comprise a closed temperature control loop.

Unless the oven 705 and microwave source 730 are tuned carefully, much of the microwave power signal 760 generated and transmitted by the microwave source 730 is reflected by the oven 705 back to the microwave source 730 where it is dissipated as useless heat. The reflected microwave signal 765 can even damage the microwave source 730. Various optional elements can be added to the system 700 to improve overall efficiency and prevent damage in the microwave source 730 caused by excessive reflected power.

As shown in FIG. 29, a directional coupler 770 couples a small portion of the reflected microwave signal 765 to a detector 775 which generates a signal indicating to the reflected power level. This signal is transmitted to a controller 710 by signal line 780. Similarly a directional coupler 790 samples a small portion of the microwave power signal 760 to the detector 795 which generates a signal related to the outgoing microwave power level. This signal is transmitted to the controller 710 by signal line 800. Given the signals from signal lines 780 and 800 indicative of the reflected and outgoing power levels respectively, the controller 710 can continuously determine how much microwave power is being transmitted into the oven 705 and how much is being reflected back to the microwave source 730.

The proportion of the microwave power reflected by the oven 705 is determined by how close the input impedance of the oven 705 matches the output impedance of the microwave source 730. The impedance match is primarily determined by the match between the microwave frequency generated by the microwave source 730 and the resonant frequency of the oven 705—the closer the respective frequencies, the less microwave energy is reflected by the oven 705. The resonant frequency of the oven 705 may vary with time. It may also vary with the temperature in the oven. Most importantly, it may vary with the type and size of the chromatographic column heated in the oven 705. By continuously varying the microwave frequency of the microwave source 730 to approximately match the resonant frequency of the oven 705, the efficiency of the microwave source 730 can be optimized. Two methods may be used to optimize efficiency and both are shown in FIG. 29.

Using the first efficiency optimization method, a controller 710 is connected to a variable frequency element 805 within the microwave source 730 by control line 810. The variable frequency element 805 is any component by which the frequency of the microwave source 730 can be varied including voltage controlled oscillators and mechanical tuning elements. The controller 710 varies the reflected microwave signal 765 by adjusting the variable frequency element 805 via the control line 810 until the reflected power signal measured on the signal line 780 is minimized, thereby indicating that the resonant frequency of the oven 705 matches the output frequency of the microwave source 730.

The second method for improving the efficiency of the system 700 is to tune the resonant frequency of the oven 705 to match the output frequency of the microwave source 730. Tuning the oven frequency can be performed using a tuning element added to the oven 705. As shown in FIG. 29, the controller 710 is connected to an oven tuning element 815 by control line 820. The oven tuning element 815 is any device capable of changing the resonant frequency of the oven 705 including, for example, a retractable metal pin protruding into the oven 705. Adjusting the length of the pin in the oven 705 adjusts the resonant frequency of the oven 705. The controller 710 varies the reflected microwave signal 765 by adjusting the oven tuning element 815 using the control line 820 until the reflected power signal measured on signal line 780 is minimized, thereby indicating that the resonant frequency of the oven 705 matches the output frequency of the microwave source 730.

Even with the reflected microwave signal 765 minimized, the microwave source 730 can be damaged or destroyed if the reflected microwave signal 765 is excessive. Damage to the microwave source 730 can be eliminated by including an optional circulator 825 in the microwave source 730 as shown in FIG. 29. The circulator 825 redirects most of the reflected microwave signal 765 into a matched load 830, which dissipates the reflected microwave signal 765.

Measuring the Temperature in the Oven

Measuring the temperature of a column in a chromatographic column microwave oven operated in vacuum conditions is more difficult than measuring the temperature of a conventional chromatographic oven. Most temperature measurement methods use: (1) a temperature sensor that is placed where it will come to thermal equilibrium with an object to be measured; and (2) metal wires to transmit information from the sensor to some remote electronics for processing. Such a configuration is problematic in a microwave oven because the metal wires can disturb the electromagnetic field within the oven and because they can act as undesirable antennas which transmit microwave radiation out of the oven. Such problems can be minimized if the signal lines from the temperature sensor run perpendicular to the electric field lines within the microwave oven. Metal wires perpendicular to the electromagnetic field lines in a microwave oven are essentially invisible to the electromagnetic field in the microwave oven. They do not disturb the field nor do they draw energy from it.

Figure 30:
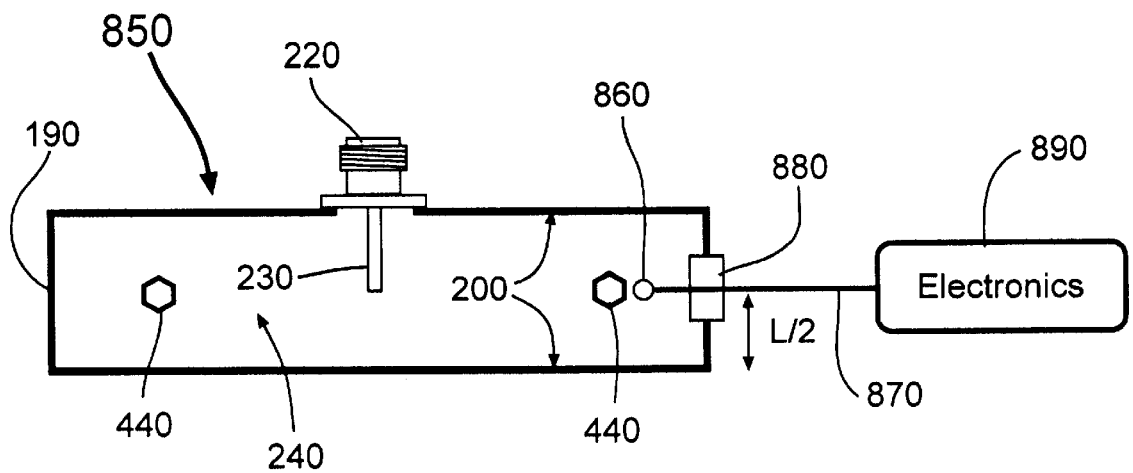
FIG. 30 is a cross-sectional view along the central axis of a chromatographic column microwave oven which utilizes a temperature sensor placed in thermal contact with the column heating assembly.

FIG. 30 shows the cross section of a chromatographic column microwave oven 850 along its central axis which utilizes a temperature sensor to measure the temperature of the column heating element 440. The oven 850 is identical to the oven 430 shown in FIG. 25 without an optional dielectric insert 250. The temperature sensor 860 is placed in contact with or in proximity to the column heating element 440 such that it is in thermal equilibrium with the column heating element 440. The temperature sensor 860 is any temperature measurement device such as a thermocouple or RTD for which proper operation requires that the measurement element must be at or near the same temperature as the object to be measured. One or more signal wires 870 transmit the signal from the temperature sensor 860 through an air tight connector 880 in the oven wall 190 to external electronics 890 for signal processing. The isofield lines in the oven 850 are circumferential as described by Eq. (4). Thus, the signal wires 860 should lie along a radial line in oven 850 so as to be perpendicular to the electric field lines. In addition, the signal lines 860 should be placed approximately halfway between the end caps 200 or at point L/2 along the side wall 190.

An alternative temperature measurement means is a non-contact, infrared temperature measurement device. An infrared temperature sensor measures the temperature of objects by analyzing the infrared radiation they give off. Such a measurement can be made remotely. Remote measurement is advantageous for a chromatographic column microwave oven because the temperature measurement means will not disturb the operation of the oven. Another advantage of infrared temperature measurement devices is that they have a faster response time than do temperature measurement means for which the temperature sensor must be in thermal equilibrium to make a measurement. A faster response time makes it easier to accurately control the temperature of a column heating element during fast temperature ramps.

Figure 31:
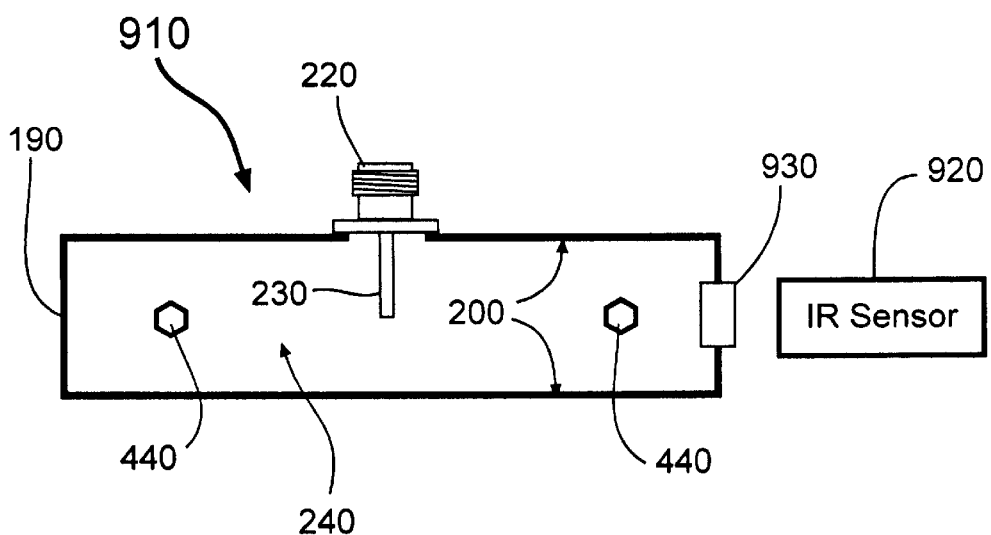
FIG. 31 is a cross-sectional view along the central axis of a chromatographic column microwave oven which utilizes an infrared temperature sensor placed outside the oven to measure the temperature of the column heating element.

FIG. 31 shows the cross section of a chromatographic column microwave oven 910 along its central axis which utilizes an infrared temperature sensor 920 to measure the temperature of column heating element 440. The oven 910 is identical to the oven 430 shown in FIG. 25 without the optional dielectric insert 250. The temperature sensor 920 is placed outside the oven 910. It is exposed to the infrared radiation given off by the column heating element 440 through an infrared transparent window 930 placed in the oven wall 190. Alternatively, the window could also be placed in one of the end caps 200. The window 930 should be sealed so that vacuum conditions can be maintained within the oven 910.

Cooling the Oven

A vacuum pump can be employed to pump the air out of the chromatographic column microwave oven so that the column heating element can be heated most efficiently. After a heating cycle has been completed, however, the column heating element must be cooled in preparation for a new analysis.

Column heating elements taught herein have low thermal mass. Similarly, chromatographic column microwave ovens taught herein are capable of high efficiency operation such that little thermal energy is dissipated into the oven itself. As a whole, very little thermal energy needs to be removed from such an oven and column heating element to cool them down. Conventional chromatographic ovens use large, high flow rate fans for cool down. Even so, they do not cool down very quickly because the ovens contain so much thermal energy. Conversely, the chromatographic column microwave ovens taught herein can be cooled rapidly with a modest flow of air. In fact, the vacuum pump itself can be used to cool the system.

Most vacuum pumps can be used to draw a steady flow rate of air when connected to the open atmosphere. Thus, to cool a chromatographic column microwave oven, the vacuum pump can be used to suck air through the oven rather than to pump air out of the oven.

Figure 32:
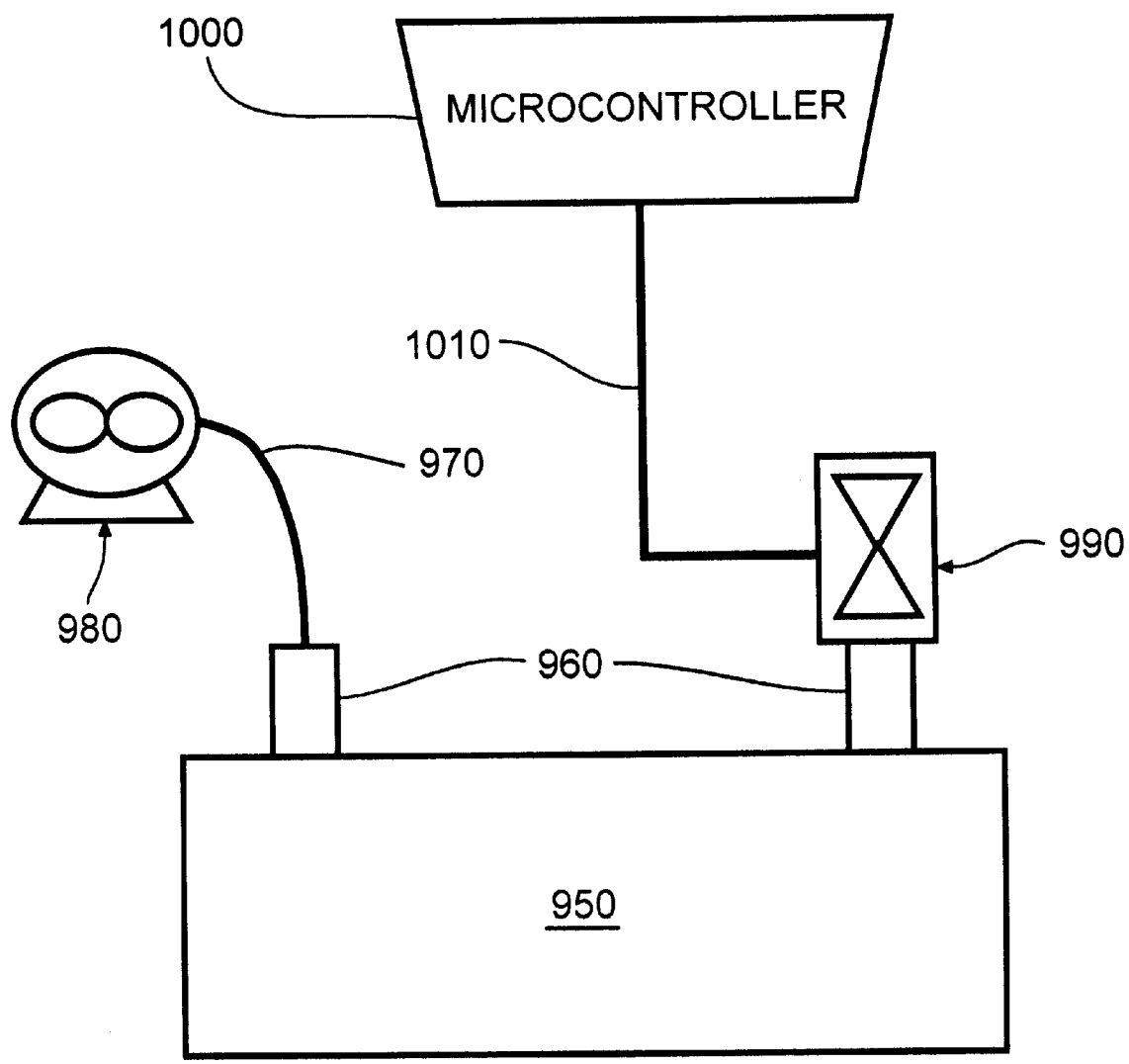
FIG. 32 shows a systems which utilizes a single vacuum pump to establish a vacuum in a chromatographic column microwave oven during a heating cycle and to cool the oven during a cooling cycle.

FIG. 32 illustrates a system utilizing one and the same vacuum pump to establish vacuum conditions during a heating cycle and to cool the oven down during a cooling cycle. The oven 950 is any oven built in accordance with the teaching of this invention. The oven 950 has two pneumatic ports 960 through which air can pass freely in and out of the oven. One port 960 is connected to an air hose 970 which in turn is connection to the vacuum pump 980. The second, inlet port 960 has a valve 990. When a vacuum condition is to be established in the oven 950, the valve 990 is closed and the vacuum pump 980 removes most of the air from the oven 950. When the oven 950 is to be cooled, the valve 990 is opened and the vacuum pump 980 draws air through the inlet port and oven 950 to remove thermal energy and thereby cool the chromatographic column. If the valve 990 is an electronic valve, it can be controlled automatically with a controller/computer 1000 via control line 1010 such that the heating and cooling cycles are fully coordinated with the other functions of the analytical instrument into which the oven system is built.

Preventing Plasma Formation in the Oven

It is possible to generate a plasma in a low pressure gas by exposing the gas to a high-strength electromagnetic field. Such a plasma can be induced in a chromatographic column microwave oven when operated in vacuum conditions because very high electromagnetic field strengths can be generated at the tip of the antenna used to transmit microwave energy into the oven. Such a plasma can be quite destructive as it can induce very high temperatures in the antenna. Consequently measures should be taken to prevent the formation of a plasma in a chromatographic column microwave oven.

Figure 33:
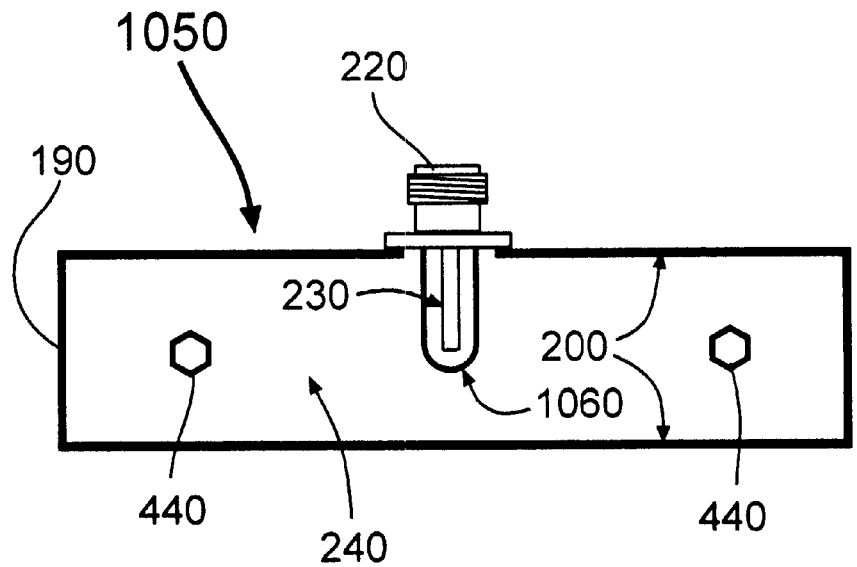
FIG. 33 is a cross-sectional view along the central axis of a chromatographic column microwave oven which utilizes a dielectric sheath on the antenna to prevent the formation of a plasma in the oven.

FIG. 33 shows the cross section of a chromatographic column microwave oven 1050 along its central axis built to prevent the formation of a plasma on antenna 230. The oven 1050 is identical to the oven 430 shown in FIG. 25, without an optional dielectric insert 250. The antenna 230 is covered at least in part with a dielectric sheath 1060 that isolates those portions of the antenna where the electromagnetic field strength is high enough to generate a plasma when vacuum conditions are present within the oven 1050. The dielectric sheath 1060 should be made of a material that is electrically non-conductive and does not absorb microwave energy, such as ceramic or polyimide.

Figure 34:
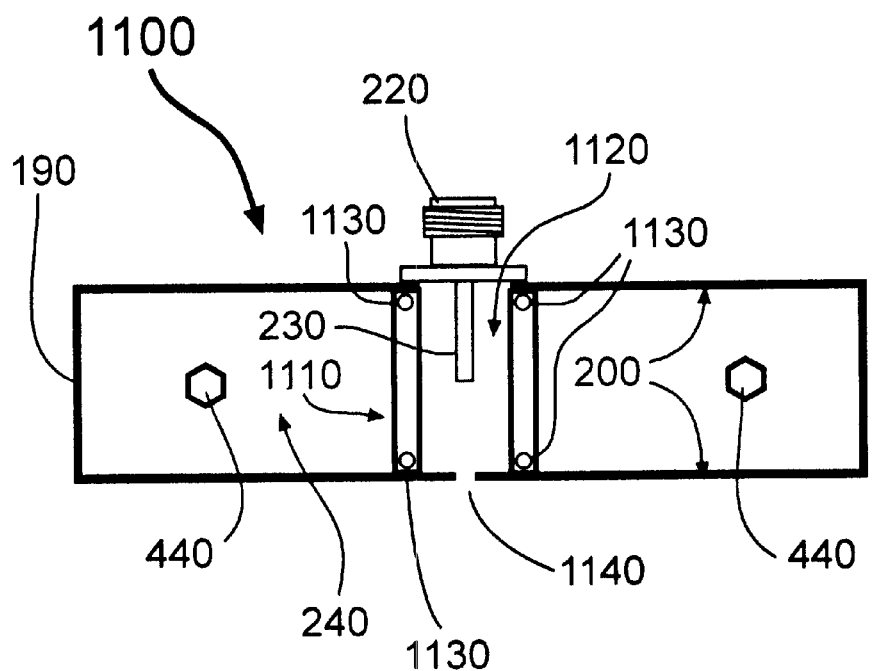
FIG. 34 is a cross-sectional view along the central axis of a chromatographic column microwave oven which utilizes a dielectric sleeve around the antenna to prevent the formation of a plasma in the oven.

FIG. 34 shows the cross section of a second chromatographic column microwave oven 1100 along its central axis built to prevent the formation of a plasma on the antenna 230. The oven 1100 is identical to the oven 430 shown in FIG. 25 without an optional dielectric insert 250. The oven 1100 contains a dielectric sleeve 1110 having an interior diameter larger than the outer diameter of antenna 230 such that there is a gap 1120 between the two. The dielectric sleeve 1110 can be a simple cylindrical tube as shown in FIG. 33 covering all or part of the antenna 230, or it could be a tube with one closed end and one open end. The dielectric sleeve 1110 should be made of a material that is electrically non-conductive and that does not absorb microwave energy such as ceramic or polyimide. The dielectric sleeve 1110 and dielectric insert 250 could be combined into a single part.

The dielectric sleeve 1110 has one or more vacuum seals 1130 to isolate the gap 1120 from the rest of the interior of oven 240. Atmospheric conditions can thus be maintained in the gap 1120 even when vacuum conditions exist elsewhere inside the oven 1100. Because the gas at the surface of antenna 230 is at atmospheric conditions and not vacuum conditions, no plasma is formed at the antenna 230 during operation. An added advantage of this oven 1100 is that air in the gap 1120 can help cool the antenna 230 and dielectric sleeve 1110 if they get hot. It is even possible to draw air through the gap 1120 to cool these parts if optional holes 1140 are opened up in the oven at either end of the dielectric sleeve 1110.

Transmitting Microwaves into the Oven

Figure 35:
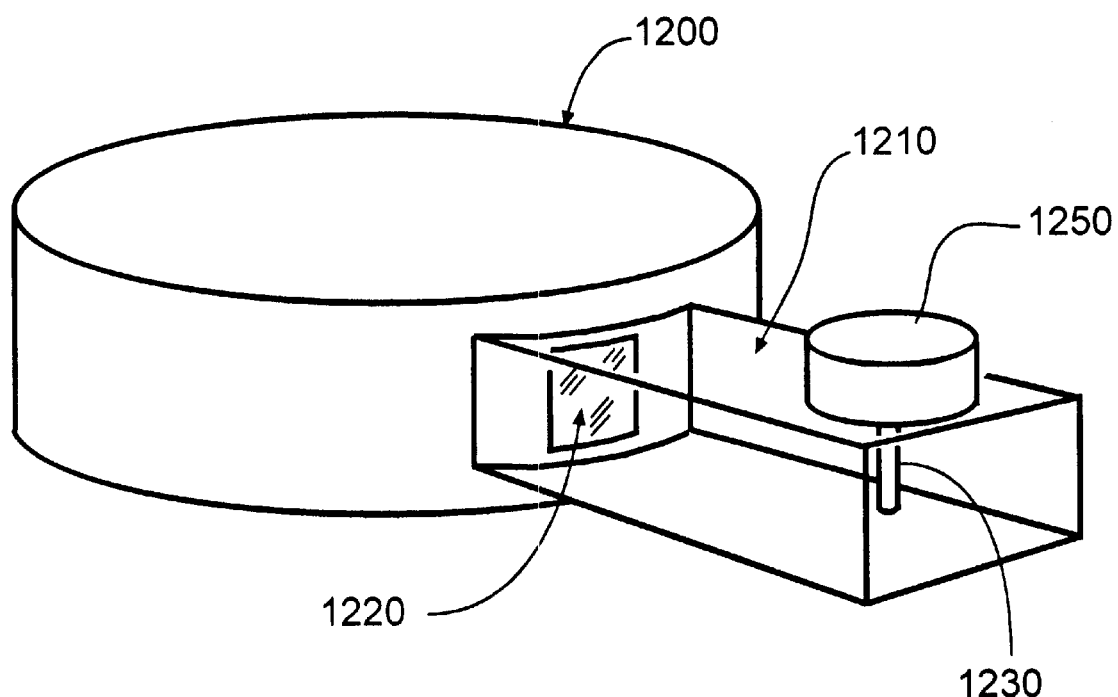
FIG. 35 shows a chromatographic column microwave oven which uses an aperture and waveguide transmitter to transmit microwave power into the oven rather than an antenna.

All chromatographic column microwave oven embodiments described herein use an antenna to transmit microwave energy directly into the oven. There are other types of transmitters by which microwave energy can be transmitted into the oven. For example, an aperture can be cut in the wall of the oven through which microwave energy can be transmitted from an external waveguide apparatus into the chromatographic microwave oven. FIG. 35 shows an external view of a chromatographic column microwave oven 1200 built with an aperture transmitter rather than an antenna transmitter. The oven 1200 can be any of the chromatographic column microwave ovens taught herein. A waveguide 1210 is connected to the external wall of oven 1200. An aperture 1220 is cut into the side wall of the oven 1200 such that electromagnetic energy propagating down the waveguide 1210 can be transmitted from the waveguide 1210 into the oven 1200 through the aperture 1220. The aperture 1220 can be an open hole or it may be a dielectric window through which electromagnetic waves can pass. Microwave energy is transmitted into the waveguide 1210 via an antenna 1230. Optionally, the antenna 1230 can be the launcher of a magnetron microwave source 1240.

Generally, any type of microwave transmitter mechanism can be used with the chromatographic column microwave ovens taught herein. The specific transmitter used to introduce microwave energy into a given oven is not a central feature of this invention.

The above disclosure sets forth a number of embodiments of the present invention. Other arrangements or embodiments, not precisely set forth, could be practiced under the teachings of the present invention and as set forth in the following claims.

We claim:

1. A microwave heating apparatus for heating a chromatographic column assembly containing a microwave absorbing material, said apparatus comprising:

a transmitter transmitting a microwave signal; and a cavity containing the chromatographic column assembly, said cavity containing an electromagnetic field in response to said microwave signal, said chromatographic column assembly extending within said cavity relative to predetermined electromagnetic field strength contours to provide a predetermined heating profile along the length of the chromatographic column assembly.

2. The microwave heating apparatus of claim 1 wherein said cavity comprises a resonant cavity.

3. The microwave heating apparatus of claim 2 further comprising a controller for approximately matching the frequency of said microwave signal to the resonant frequency of said cavity.

4. The microwave heating apparatus of claim 1 wherein said cavity further comprises an infrared-reflective interior surface.

5. The microwave heating apparatus of claim 1 further comprising:

an inlet port leading into said cavity;

an outlet port leading from said cavity;

a pump withdrawing air from within said cavity through said outlet port; and a valve regulating the flow of air through said inlet port into said cavity, wherein said valve is closed during heating of the oven so that said pump creates at least a partial vacuum within said cavity, and wherein said valve is opened after heating of the oven so that said pump draws air through said inlet port and said cavity to cool the chromatographic column assembly.

6. The microwave heating apparatus of claim 1 wherein said transmitter comprises an antenna within said cavity, and further comprising a dielectric material surrounding at least a portion of said antenna to suppress plasma formation.

7. The microwave heating apparatus of claim 1 further comprising an infrared temperature sensor for measuring the temperature of the chromatographic column assembly within said cavity.

8. The microwave heating apparatus of claim 1 further comprising a temperature sensor within said cavity for measuring the temperature of the chromatographic column assembly, said temperature sensor having signal lines extending substantially perpendicular to the electric field lines within said cavity caused by said microwave signal.

9. The microwave heating apparatus of claim 1 further comprising a controller adjusting the microwave power delivered to said cavity to achieve a desired temperature for the chromatographic column assembly.

10. The microwave heating apparatus of claim 1 further comprising:
    a microwave source powering said transmitter; and
    a circulator protecting said microwave source from reflected microwave energy.

11. A microwave heating apparatus for heating a chromatographic column assembly containing a microwave absorbing material and having a coiled column with a plurality of loops extending about an axis, said apparatus comprising:
    a transmitter transmitting a microwave signal; and
    a cavity containing the coiled column, said cavity containing an electromagnetic field in response to said microwave signal, said electromagnetic field providing a predetermined heating profile along each individual loop of the coiled column and a predetermined heating profile along the axis of the coiled column.

12. The microwave heating apparatus of claim 11 wherein said cavity comprises a resonant cavity.

13. The microwave heating apparatus of claim 12 further comprising a controller for approximately matching the frequency of said microwave signal to the resonant frequency of said cavity.

14. The microwave heating apparatus of claim 11 wherein said cavity further comprises an infrared-reflective interior surface.

15. The microwave heating apparatus of claim 11 further comprising:
    an inlet port leading into said cavity;
    an outlet port leading from said cavity;
    a pump withdrawing air from within said cavity through said outlet port; and
    a valve regulating the flow of air through said inlet port into said cavity, wherein said valve is closed during heating of the oven so that said pump creates at least a partial vacuum within said cavity, and wherein said valve is opened after heating of the oven so that said pump draws air through said inlet port and said cavity to cool the chromatographic column assembly.

16. The microwave heating apparatus of claim 11 wherein said transmitter comprises an antenna within said cavity, and further comprising a dielectric material surrounding at least a portion of said antenna to suppress plasma formation.

17. The microwave heating apparatus of claim 11 further comprising an infrared temperature sensor for measuring the temperature of the chromatographic column assembly within said cavity.

18. The microwave heating apparatus of claim 11 further comprising a temperature sensor within said cavity for measuring the temperature of the chromatographic column assembly, said temperature sensor having signal lines extending substantially perpendicular to the electric field lines within said cavity caused by said microwave signal.

19. The microwave heating apparatus of claim 11 further comprising a controller adjusting the microwave power delivered to said cavity to achieve a desired temperature for the chromatographic column assembly.

20. The microwave heating apparatus of claim 11 further comprising:
    a microwave source powering said transmitter; and
    a circulator protecting said microwave source from reflected microwave energy.

21. A microwave heating apparatus for heating a chromatographic column assembly containing a microwave absorbing material and having a coiled column with a plurality of loops, said apparatus comprising:
    a substantially cylindrical resonant cavity containing the coiled column and supporting the coiled column in a radially symmetrical arrangement about a central axis; and
    a transmitter transmitting a microwave signal into said resonant cavity to produce an electromagnetic field within said resonant cavity that is radially symmetric about said central axis and has a predetermined gradient in the axial direction.

22. The microwave heating apparatus of claim 21 further comprising a controller approximately matching the frequency of said microwave signal to the resonant frequency of said cavity.

23. The microwave heating apparatus of claim 21 wherein said cavity further comprises an infrared-reflective interior surface.

24. The microwave heating apparatus of claim 21 further comprising:
    an inlet port leading into said cavity;
    an outlet port leading from said cavity;
    a pump withdrawing air from within said cavity through said outlet port; and
    a valve regulating the flow of air through said inlet port into said cavity, wherein said valve is closed during heating of the oven so that said pump creates at least a partial vacuum within said cavity, and wherein said valve is opened after heating of the oven so that said pump draws air through said inlet port and said cavity to cool the chromatographic column assembly.

25. The microwave heating apparatus of claim 21 wherein said transmitter comprises an antenna within said cavity, and further comprising a dielectric material surrounding at least a portion of said antenna to suppress plasma formation.

26. The microwave heating apparatus of claim 21 further comprising an infrared temperature sensor for measuring the temperature of the chromatographic column assembly within said cavity.

27. The microwave heating apparatus of claim 21 further comprising a temperature sensor within said cavity for measuring the temperature of the chromatographic column assembly, said temperature sensor having signal lines extending substantially perpendicular to the electric field lines within said cavity caused by said microwave signal.

28. The microwave heating apparatus of claim 21 further comprising a controller adjusting the microwave power delivered to said cavity to achieve a desired temperature for the chromatographic column assembly.

29. The microwave heating apparatus of claim 21 further comprising:
    a microwave source powering said transmitter; and
    a circulator protecting said microwave source from reflected microwave energy.

* * * * *

UNITED STATES PATENT AND TRADEMARK OFFICE
CERTIFICATE OF CORRECTION

PATENT NO. : 6,157,015
DATED : December 5, 2000
INVENTOR(S) : Gaisford et al.

It is certified that error appears in the above-identified patent and that said Letters Patent is hereby corrected as shown below:

Column 5, line 64, replace "the oven is an" with -the oven is a-
Column 7, line 1, replace "an system" with -a system-
Column 8, line 67, replace "an spherical" with -a spherical-
Column 9, line 56, replace "two right" with - to right -
Column 10, line 34, replace "120" with -110- ; "130" with -120-
Column 10, line 41, replace "of the these" with -of these-
Column 10, line 59, replace "propagation There" with - propagation. There -
Column 26, line 2, replace "700" with -705-
Column 29, line 2, replace "connection" with -connected-
Column 29, line 3, replace "has a valve" with -comprises a valve-
Column 30, line 22, replace "1240" with -1250-

Signed and Sealed this

Twenty-fourth Day of April, 2001

Attest:

NICHOLAS P. GODICI

Attesting Officer

Acting Director of the United States Patent and Trademark Office